United States Patent [19]
Wong et al.

[11] Patent Number: 6,046,331
[45] Date of Patent: Apr. 4, 2000

[54] IMIDAZOLONES AND THEIR USE IN TREATING BENIGN PROSTATIC HYPERPLASIA AND OTHER DISORDERS

[75] Inventors: Wai C. Wong, Livingston, N.J.; T. G. Murali Dhar, Newtown, Pa.; Charles Gluchowski, Danville, Calif.

[73] Assignee: Synaptic Pharmaceutical Corporation, Paramus, N.J.

[21] Appl. No.: 09/213,078

[22] Filed: Dec. 17, 1998

[51] Int. Cl.[7] .................. C07D 403/00; C07D 411/00; A61K 31/495; A61K 31/44
[52] U.S. Cl. .................. 544/370; 514/255; 514/341; 546/210
[58] Field of Search .................. 544/370; 546/210; 514/255, 341

[56] References Cited

U.S. PATENT DOCUMENTS

| | | | |
|---|---|---|---|
| 5,227,486 | 7/1993 | Merce-Vidal et al. | 544/295 |
| 5,731,331 | 3/1998 | Merce-Vidal et al. | 514/341 |
| 5,760,234 | 6/1998 | Yuan et al. | 546/208 |
| 5,776,937 | 7/1998 | Gante et al. | 514/252 |
| 5,872,136 | 2/1999 | Anthony et al. | 514/341 |

FOREIGN PATENT DOCUMENTS

| | | | |
|---|---|---|---|
| 0379990 | 8/1990 | European Pat. Off. | 546/210 |
| 61-53281 | 3/1986 | Japan | 546/210 |
| 61-191681 | 8/1986 | Japan . | |
| WO9721439 | 6/1997 | WIPO . | |

*Primary Examiner*—Floyd D. Higel
*Attorney, Agent, or Firm*—John P. White; Cooper & Dunham LLP

[57] ABSTRACT

This invention is directed to imidazolones which are selective antagonists for human $\alpha_{1a}$ receptors. This invention is also related to uses of these compounds for lowering intraocular pressure, inhibiting cholesterol synthesis, relaxing lower urinary tract tissue, the treatment of benign prostatic hyperplasia, impotency, cardiac arrhythmia, sympathetic mediated pain, migraine, and for the treatment of any disease where the antagonism of the $\alpha_{1a}$ receptor may be useful. The invention further provides a pharmaceutical composition comprising a therapeutically effective amount of the above-defined compounds and a pharmaceutically acceptable carrier.

42 Claims, 14 Drawing Sheets

Compound 1

Compound 2

Compound 3

Compound 4

Compound 5

Compound 6

Compound 7

Compound 8

Compound 9

Compound 10

Compound 11

Compound 12

Compound 13

Compound 14

Compound 15

Compound 16

Compound 17

Compound 18

Compound 19

Compound 20

Compound 21

Compound 22

Compound 23

Compound 24

Compound 25

Compound 26

Compound 27

Compound 28

Compound 29

Compound 30

Compound 31

Compound 32

Compound 33

Compound 34

Compound 35

Compound 36

Compound 37

Compound 38

Compound 39

Compound 40

IMIDAZOLONES AND THEIR USE IN TREATING BENIGN PROSTATIC HYPERPLASIA AND OTHER DISORDERS

Throughout this application, various references are referred to within parentheses. Disclosures of these publications in their entireties are hereby incorporated by reference into this application to more fully describe the state of the art to which this invention pertains.

BACKGROUND OF THE INVENTION

The designation "$\alpha_{1a}$" is the appellation recently approved by the IUPHAR Nomenclature Committee for the previously designated "$\alpha_{1c}$" cloned subtype as outlined in the Pharmacological Reviews (Hieble, et al. (1995) *Pharmacological Reviews* 47: 267–270). The designation $\alpha_{1a}$ is used throughout this application and the supporting tables and figures to refer to this receptor subtype. At the same time, the receptor formerly designated $\alpha_{1a}$ was renamed $\alpha_{1d}$. The new nomenclature is used throughout this application. Stable cell lines expressing these receptors are described herein; however, these cell lines were deposited with the American Type Culture Collection (ATCC) under the old nomenclature (infra).

Benign Prostatic Hyperplasia (BPH), also called Benign Prostatic Hypertrophy, is a progressive condition which is characterized by a nodular enlargement of prostatic tissue resulting in obstruction of the urethra. This results in increased frequency of urination, nocturia, a poor urine stream, and hesitancy or delay in starting the urine flow. Chronic consequences of BPH can include hypertrophy of bladder smooth muscle, a decompensated bladder, and an increased incidence of urinary tract infection. The specific biochemical, histological, and pharmacological properties of the prostate adenoma leading to the bladder outlet obstruction are not yet known. However, the development of BPH is considered to be an inescapable phenomenon for the aging male population. BPH is observed in approximately 70% of males over the age of 70. Currently, in the United States, the method of choice for treating BPH is surgery (Lepor, H., *Urol. Clinics North Amer.*, 17: 651, 1990). Over 400,000 prostatectomies are performed annually (data from 1986). The limitations of surgery for treating BPH include the morbidity rate of an operative procedure in elderly men, persistence or recurrence of obstructive and irritative symptoms, as well as the significant cost of surgery. A medicinal alternative to surgery is clearly very desirable.

α-Adrenergic receptors (McGrath et al., *Med. Res. Rev.* 9: 407–533, 1989) are specific neuroreceptor proteins located in the peripheral and central nervous systems on tissues and organs throughout the body. These receptors are important switches for controlling many physiological functions and, thus, represent important targets for drug development. In fact, many α-adrenergic drugs have been developed over the past 40 years. Examples include clonidine, phenoxybenzamine and prazosin (for treatment of hypertension), naphazoline (a nasal decongestant), and apraclonidine (for treatment of glaucoma). α-adrenergic drugs can be broken down into two distinct classes: agonists (e.g., clonidine and naphazoline), which mimic the receptor activation properties of the endogenous neurotransmitter norepinephrine, and antagonists (e.g., phenoxybenzamine and prazosin), which act to block the effects of norepinephrine. Many of these drugs are effective, but also produce unwanted side effects (e.g., clonidine produces dry mouth and sedation in addition to its antihypertensive effects).

During the past 15 years, a more precise understanding of α-adrenergic receptors and their drugs has evolved through increased scientific scrutiny. Prior to 1977, only one α-adrenergic receptor was known to exist. Between 1977 and 1988, it was accepted by the scientific community that at least two α-adrenergic receptors, $\alpha_1$ and $\alpha_2$, existed in the central and peripheral nervous systems. Since 1988, new techniques in molecular biology have led to the identification of at least six α-adrenergic receptors which exist throughout the central and peripheral nervous systems: $\alpha_{1a}$ (new nomenclature), $\alpha_{1b}$, $\alpha_{1d}$ (new nomenclature), $\alpha_{2a}$, $\alpha_{2b}$ and $\alpha_{2c}$ (Bylund, D. B., *FASEB J.* 6: 832, 1992). In many cases, it is not known precisely which physiological responses in the body are controlled by each of these receptors. In addition, current α-adrenergic drugs are not selective for any particular α-adrenergic receptor. Many of these drugs produce untoward side effects that may be attributed to their poor α-adrenergic receptor selectivity.

Since the mid 1970's, nonselective α-antagonists have been prescribed to treat BPH. In 1976, M. Caine et al. (*Brit. J. Urol.* 48: 255, 1976) reported that the nonselective α-antagonist phenoxybenzamine was useful in relieving the symptoms of BPH. This drug may produce its effects by interacting with α-receptors located on the prostate. However, this drug also produces significant side effects such as dizziness and asthenia, which severely limit its use in treating patients on a chronic basis. More recently, the α-adrenergic antagonists prazosin and terazosin have also been found to be useful for treating BPH. However, these drugs also produce untoward side effects. It has recently been discovered that the $\alpha_{1a}$ receptor is responsible for mediating the contraction of human prostate smooth muscle (Gluchowski, C. et al., WO 94/10989, 1994; Forray, C. et al., *Mol. Pharmacol.* 45: 703, 1994). This discovery indicates that the $\alpha_{1a}$ antagonists may be effective agents for the treatment of BPH with decreased side effects. Further studies have indicated that the $\alpha_{1a}$ receptor may also be present in other lower urinary tract tissues, such as urethral smooth muscle (Ford et al., *Br. J. Pharmacol.* 114: 24P, 1995).

This invention is directed to imidazolones which are selective antagonists for cloned human $\alpha_{1a}$ receptors. This invention is also related to uses of these compounds for lowering intraocular pressure (Zhan, et al., *Ophthalmol. Vis. Sci.* 34: Abst. #1133, 928, 1993), inhibiting cholesterol synthesis (D'Eletto and Javitt, *J. Cardiovascular Pharmacol.* 13: (Suppl. 2) S1–S4, 1989), benign prostatic hyperplasia, impotency (Milne and Wyllie, EP 0 459 666 A2, 1991), sympathetically mediated pain (Campbell, WO 92/14453, 1992), cardiac arrhythmia (Spiers, et al., *J. Cardiovascular Pharmacol.* 16: 824–830, 1990), migraine (K. A. Vatz, *Headache* 37: 107–108, 1997) and for the treatment of any disease where antagonism of the $\alpha_{1a}$ receptor may be useful.

SUMMARY OF THE INVENTION

This invention is directed to a compound having the structure:

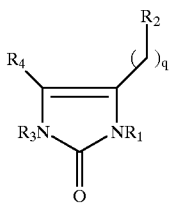

where R₂ is aryl or heteroaryl; wherein the aryl or heteroaryl may be substituted with one or more of F; Cl; Br; I; —CN; —NO₂; —N(R₈)₂; —SO₂R₈; —SO₂N(R₈)₂; —(CH₂)$_n$C(Y)R₈; —(CH₂)$_n$YR₈; —(CH₂)$_n$C(Y)N(R₈)₂; —(CH₂)$_n$CO₂R₈; methylenedioxy; straight chained or branched C₁–C₇ alkyl, monofluoroalkyl, polyfluoroalkyl, aminoalkyl, or carboxamidoalkyl; straight chained or branched C₂–C₇ alkenyl or alkynyl; C₃–C₇ cycloalkyl; or C₅–C₇ cycloalkenyl;

where R₃ is independently H; straight chained or branched C₁–C₇ alkyl, alkoxyalkyl, monofluoroalkyl, or polyfluoroalkyl;

where R₄ is H, —(CH₂)$_t$YR₈, —(CH₂)$_t$C(Y)N(R₈)₂, —(CH₂)$_t$C(Y)R₈, —(CH₂)$_t$CO₂R₈, —(CH₂)$_t$N(R₈)₂, —(CH₂)$_t$CN, —C(Y)R₈, —C(Y)N(R₈)₂, —CO₂R₈, straight chained or branched C₁–C₇ alkyl, straight chained or branched C₂–C₇ alkenyl or alkynyl, C₃–C₇ cycloalkyl, C₅–C₇ cycloalkenyl, or phenyl or benzyl; wherein the phenyl or benzyl may be substituted with one or more of F; Cl; Br; I; —CN; —NO₂; —N(R₈)₂; —SO₂R₈; —SO₂N(R₈)₂; —(CH₂)$_n$C(Y)R₈; —(CH₂)$_n$YR₈; —(CH₂)$_n$C(Y)N(R₈)₂; —(CH₂)$_n$CO₂R₈; methylenedioxy; straight chained or branched C₁–C₇ alkyl, monofluoroalkyl, polyfluoroalkyl, aminoalkyl, or carboxamidoalkyl; straight chained or branched C₂–C₇ alkenyl or alkynyl; C₃–C₇ cycloalkyl; or C₅–C₇ cycloalkenyl;

where each R₈ is independently H, straight chained or branched C₁–C₇ alkyl, straight chained or branched C₂–C₇ alkenyl or alkynyl, C₃–C₇ cycloalkyl, C₅–C₇ cycloalkenyl, or polyfluoroalkyl;

where q is an integer from 0 to 4 inclusive;

where each n independently is an integer from 0 to 7 inclusive;

where each t independently is an integer from 1 to 4 inclusive;

where each Y is independently O or S;

where R₁ is

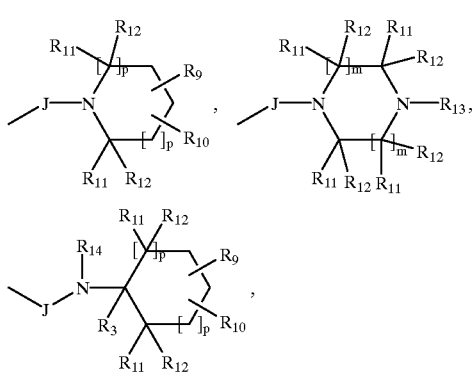

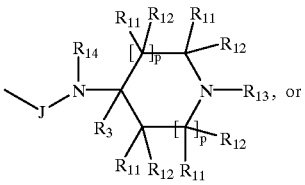

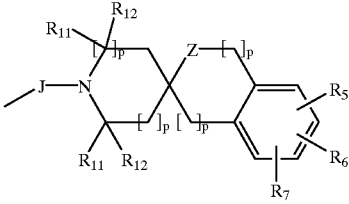

wherein R₅, R₆, and R₇ independently are H; F; Cl; Br; I; —CN; —NO₂; —N(R₈)₂; —SO₂R₈; —(CH₂)$_n$C(Y)R₈; —(CH₂)$_n$YR₈; —(CH₂)$_n$C(Y)N(R₈)₂; —(CH₂)$_n$CO₂R₈; —SO₂N(R₈)₂; methylenedioxy; straight chained or branched C₁–C₇ alkyl, monofluoroalkyl, polyfluoroalkyl, aminoalkyl, or carboxamidoalkyl; straight chained or branched C₂–C₇ alkenyl or alkynyl; C₃–C₇ cycloalkyl; or C₅–C₇ cycloalkenyl;

wherein each R₉ is H; straight chained or branched C₁–C₇ alkyl, hydroxyalkyl, aminoalkyl, alkoxyalkyl, monofluoroalkyl, or polyfluoroalkyl; straight chained or branched C₂–C₇ alkenyl or alkynyl; C₃–C₇ cycloalkyl, monofluorocycloalkyl, or polyfluorocycloalkyl; C₅–C₇ cycloalkenyl; or aryl or heteroaryl; wherein the aryl or heteroaryl may be substituted with one or more of F; Cl; Br; I; —(CH₂)$_n$YR₈; —(CH₂)$_n$C(Y)₈; —(CH₂)$_n$C(Y)N(R₈)₂; —(CH₂)$_n$CO₂R₈; —CN; —NO₂; —N(R₈)₂; —SO₂R₈; —SO₂N(R₈)₂; methylenedioxy; straight chained or branched C₁–C₇ alkyl, monofluoroalkyl, or polyfluoroalkyl; straight chained or branched C₂–C₇ alkenyl or alkynyl; C₃–C₇ cycloalkyl, monofluorocycloalkyl, or polyfluorocycloalkyl; or C₅–C₇ cycloalkenyl;

wherein each R₁₀ is H; F; —OH; —(CH₂)$_n$C(Y)R₈; —(CH₂)$_n$YR₈; —(CH₂)$_n$C(Y)N(R₈)₂; —(CH₂)$_n$CO₂R₈; —CN; —NO₂; —N(R₈)₂; aryl or heteroaryl; straight chained or branched C₁–C₇ alkyl, hydroxyalkyl, aminoalkyl, carboxamidoalkyl, alkoxyalkyl, monofluoroalkyl, or polyfluoroalkyl; straight chained or branched C₂–C₇ alkenyl or alkynyl; C₃–C₇ cycloalkyl, monofluorocycloalkyl, or polyfluorocycloalkyl; or C₅–C₇ cycloalkenyl; wherein the alkyl, hydroxyalkyl, alkoxyalkyl, aminoalkyl, carboxamidoalkyl, alkenyl, alkynyl, cycloalkyl or cycloalkenyl may be substituted with one or more aryl or heteroaryl; wherein the aryl or heteroaryl may be substituted with one or more of F; Cl; Br; I; —(CH₂)$_n$YR₈; —(CH₂)$_n$C(Y)R₈; —(CH₂)$_n$C(Y)N(R₈)₂; —(CH₂)$_n$CO₂R₈; —CN; —NO₂; —N(R₈)₂; —SO₂R₈; —SO₂N(R₈)₂; methylenedioxy; straight chained or branched C₁–C₇ alkyl, monofluoroalkyl, or polyfluoroalkyl; straight chained or branched C₂–C₇ alkenyl or alkynyl; C₃–C₇ cycloalkyl, monofluorocycloalkyl, or polyfluorocycloalkyl; or C₅–C₇ cycloalkenyl;

wherein each R₁₁ is independently H, —(CH₂)$_t$YR₈, —(CH₂)$_t$C(Y)N(R₈)₂, —(CH₂)$_t$C(Y)R₈, —(CH₂)$_t$CO₂R₈, —(CH₂)$_t$N(R₈)₂, —(CH₂)$_t$CN, —C(Y)R₈, —C(Y)N(R₈)₂, —CO₂R₈, straight chained or branched C₁–C₇ alkyl, straight chained or branched C₂–C₇ alkenyl or alkynyl, C₃–C₇ cycloalkyl, or C₅–C₇ cycloalkenyl;

wherein each R₁₂ is independently H, —(CH₂)$_t$YR₈, —(CH₂)$_t$C(Y)N(R₈)₂, —(CH₂)$_t$C(Y)R₈, —(CH₂)$_t$CO₂R₈, —(CH₂)$_t$N(R₈)₂, —(CH₂)$_t$CN, straight chained or branched $C_1$–$C_7$ alkyl, straight chained or branched $C_2$–$C_7$ alkenyl or alkynyl, $C_3$–$C_7$ cycloalkyl, or $C_5$–$C_7$ cycloalkenyl;

wherein $R_{13}$ is H, $C_1$–$C_7$ alkyl, —C(O)$R_2$, aryl or heteroaryl, $C_1$–$C_7$ alkyl substituted with one or two aryl, or $C_1$–$C_7$ alkyl substituted with one or two heteroaryl; wherein the aryl or heteroaryl may be substituted with one or more of F; Cl; Br; I; —CN; —NO$_2$; —N($R_8$)$_2$; —SO$_2$$R_8$; —SO$_2$N($R_8$)$_2$; —(CH$_2$)$_n$C(Y)$R_8$; —(CH$_2$)$_n$Y$R_8$; —(CH$_2$)$_n$C(Y)N($R_8$)$_2$; —(CH$_2$)$_n$CO$_2$$R_8$; methylenedioxy; straight chained or branched $C_1$–$C_7$ alkyl, monofluoroalkyl, polyfluoroalkyl, or carboxamidoalkyl; straight chained or branched $C_2$–$C_7$ aminoalkyl, alkenyl, or alkynyl; $C_3$–$C_7$ cycloalkyl; or $C_5$–$C_7$ cycloalkenyl;

wherein $R_{14}$ is H, straight chained or branched $C_1$–$C_7$ alkyl; wherein Z is O, S, N$R_{14}$, CO, CH$_2$,

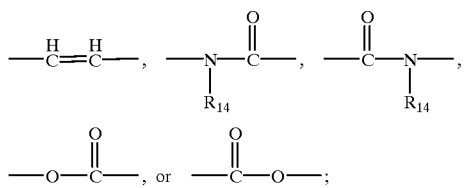

wherein each m is independently 1 or 2;

where each p is independently an integer from 0 to 2 inclusive;

wherein J is

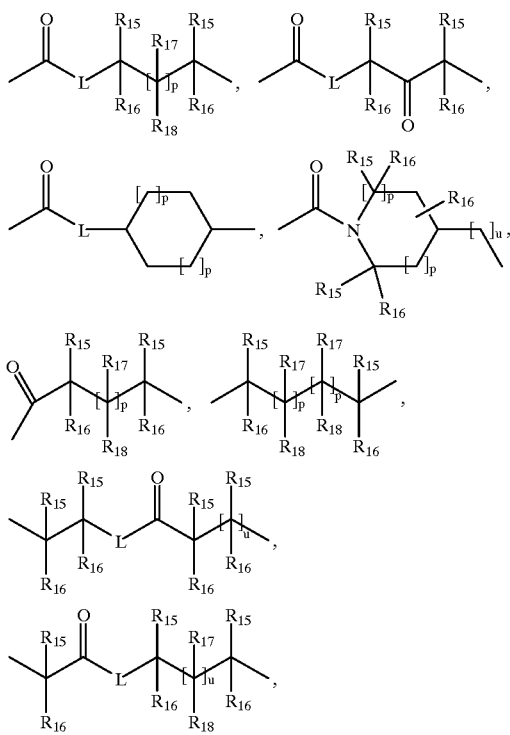

or $C_2$–$C_7$ alkenyl;

wherein each $R_{15}$ is independently H, —(CH$_2$)$_t$Y$R_8$, —(CH$_2$)$_t$C(Y)N($R_8$)$_2$, —(CH$_2$)$_t$C(Y)$R_8$, —(CH$_2$)$_t$CO$_2$$R_8$, —(CH$_2$)$_t$N($R_8$)$_2$, —(CH$_2$)$_t$CN, —C(Y)$R_8$, —C(Y)N($R_8$)$_2$, —CO$_2$$R_8$, straight chained or branched $C_1$–$C_7$ alkyl, straight chained or branched $C_2$–$C_7$ alkenyl or alkynyl, $C_3$–$C_7$ cycloalkyl, or $C_5$–$C_7$ cycloalkenyl;

wherein each $R_{16}$ is independently H, —(CH$_2$)$_t$Y$R_8$, —(CH$_2$)$_t$C(Y)N($R_8$)$_2$, —(CH$_2$)$_t$C(Y)$R_8$, —(CH$_2$)$_t$CO$_2$$R_8$, —(CH$_2$)$_t$N($R_8$)$_2$, —(CH$_2$)$_t$CN, straight chained or branched $C_1$–$C_7$ alkyl, straight chained or branched $C_2$–$C_7$ alkenyl or alkynyl, $C_3$–$C_7$ cycloalkyl, or $C_5$–$C_7$ cycloalkenyl;

wherein each $R_{17}$ is independently H; F; —(CH$_2$)$_t$Y$R_8$; —(CH$_2$)$_t$C(Y)N($R_8$)$_2$; —(CH$_2$)$_t$C(Y)$R_8$; —(CH$_2$)$_t$CO$_2$$R_8$; —(CH$_2$)$_t$N($R_8$)$_2$; —(CH$_2$)$_t$CN; —C(Y)$R_8$; —C(Y)N($R_8$)$_2$; —CO$_2$$R_8$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl;

wherein each $R_{18}$ is independently H; F; —(CH$_2$)$_t$Y$R_8$; —(CH$_2$)$_t$C(Y)N($R_8$)$_2$; —(CH$_2$)$_t$C(Y)$R_8$; —(CH$_2$)$_t$CO$_2$$R_8$; —(CH$_2$)$_t$N($R_8$)$_2$; —(CH$_2$)$_t$CN; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl;

wherein L is S, O, or N($R_8$);

wherein u is an integer from 0 to 1 inclusive;

or a pharmaceutically acceptable salt thereof.

This invention provides for a pharmaceutical composition comprising a therapeutically effective amount of any one of the compounds described herein and a pharmaceutically acceptable carrier.

This invention provides for a method of treating a subject suffering from benign prostatic hyperplasia which comprises administering to the subject an amount of any one of the compounds described herein effective to treat benign prostatic hyperplasia.

This invention provides for a method of treating a subject suffering from high intraocular pressure which comprises administering to the subject an amount of any one of the compounds described herein effective to lower intraocular pressure.

This invention provides for a method of treating a subject suffering from a disorder associated with high cholesterol which comprises administering to the subject an amount of any one of the compounds described herein effective to inhibit cholesterol synthesis.

This invention provides for a method of treating a subject suffering from cardiac arrhythmia which comprises administering to the subject an amount of any one of the compounds described herein effective to treat cardiac arrhythmia.

This invention provides for a method of treating a subject suffering from impotency which comprises administering to the subject an amount of any one of the compounds described herein effective to treat impotency.

This invention provides for a method of treating a subject suffering from sympathetically mediated pain which comprises administering to the subject an amount of any one of the compounds described herein effective to treat sympathetically mediated pain.

This invention provides for a method of treating a subject suffering from migraine which comprises administering to the subject an amount of any one of the compounds described herein effective to treat migraine.

This invention provides for a method of treating a disease which is susceptible to treatment by antagonism of the $\alpha_{1a}$ receptor which comprises administering to the subject an amount of any one of the compounds described herein effective to treat the disease.

This invention provides for a method of treating a subject suffering from benign prostatic hyperplasia which comprises administering to the subject an amount of any one of the compounds described herein in combination with a 5-alpha reductase inhibitor effective to treat benign prostatic hyperplasia.

This invention provides for a pharmaceutical composition comprising a therapeutically effective amount of any one of the compounds described herein in combination with a therapeutically effective amount of finasteride and a pharmaceutically acceptable carrier.

This invention provides for a method of relaxing lower urinary tract tissue which comprises contacting the lower urinary tract tissue with an amount of any one of the compounds described herein effective to relax lower urinary tract tissue.

This invention provides for a method of relaxing lower urinary tract tissue in a subject which comprises administering to the subject an amount of any one of the compounds described herein effective to relax lower urinary tract tissue.

This invention provides for a pharmaceutical composition made by combining a therapeutically effective amount of any one of the compounds described herein and a pharmaceutically acceptable carrier.

This invention provides for a pharmaceutical composition made by combining a therapeutically effective amount of any one of the compounds described herein with a therapeutically effective amount of finasteride and a pharmaceutically acceptable carrier.

This invention provides for a process for making a pharmaceutical composition comprising combining a therapeutically effective amount of any one of the compounds described herein and a pharmaceutically acceptable carrier.

This invention provides for a process for making a pharmaceutical composition comprising combining a therapeutically effective amount of any one of the compounds described herein with a therapeutically effective amount of finasteride and a pharmaceutically acceptable carrier.

BRIEF DESCRIPTION OF THE FIGURES

FIGS. 1A–1N show the structures of the compounds described herein in the Examples.

DETAILED DESCRIPTION OF THE INVENTION

Figure 1A:
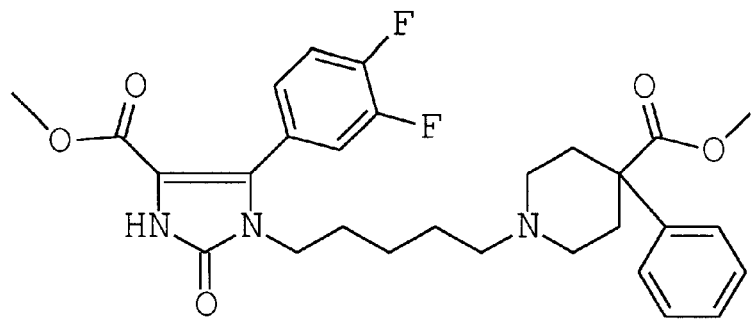
FIGS. 1A–1N
Figure 1A:
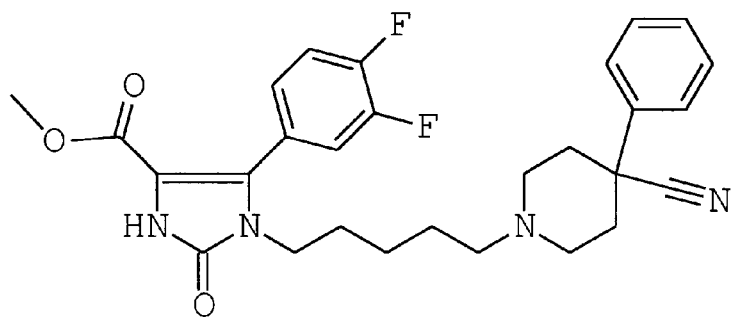
Figure 1A:
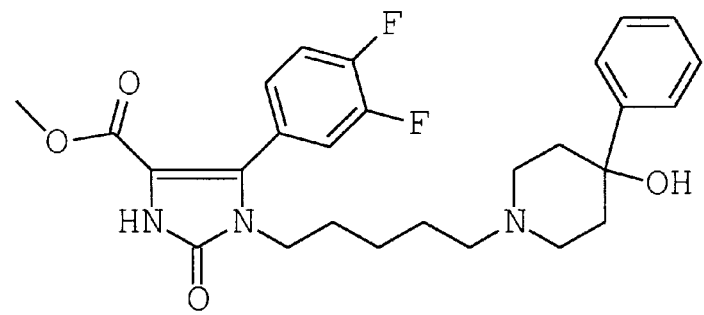
Figure 1B:
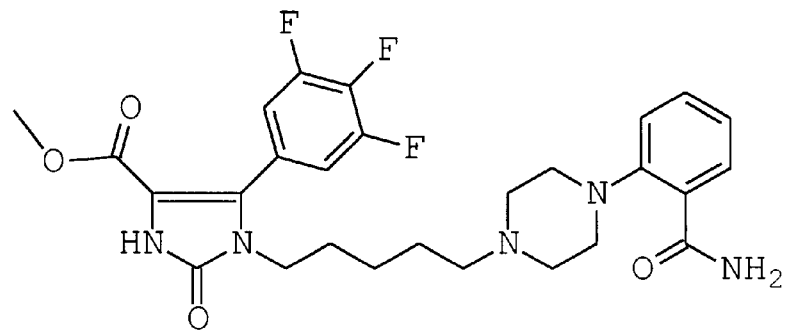
Figure 1B:
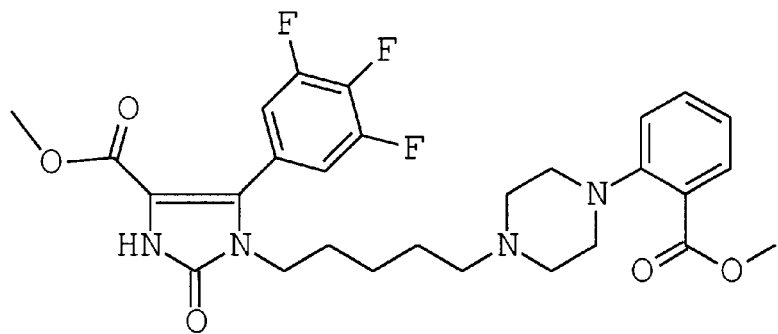
Figure 1B:
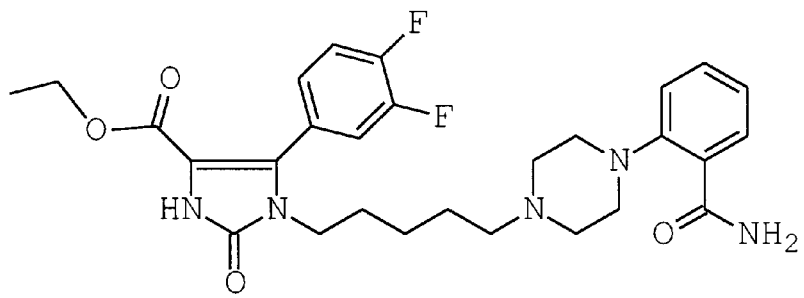
Figure 1C:
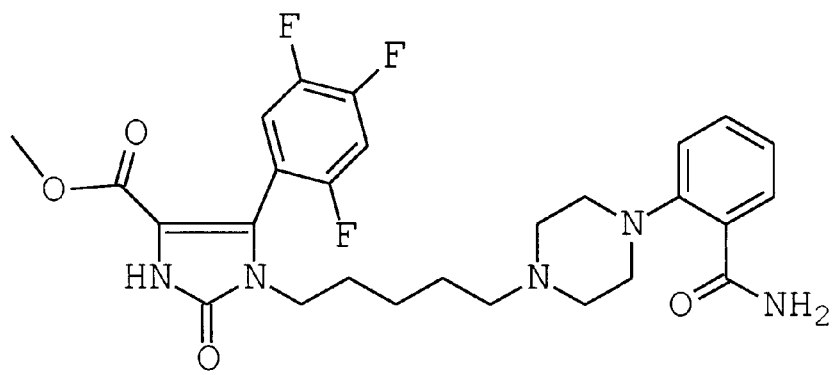
Figure 1C:
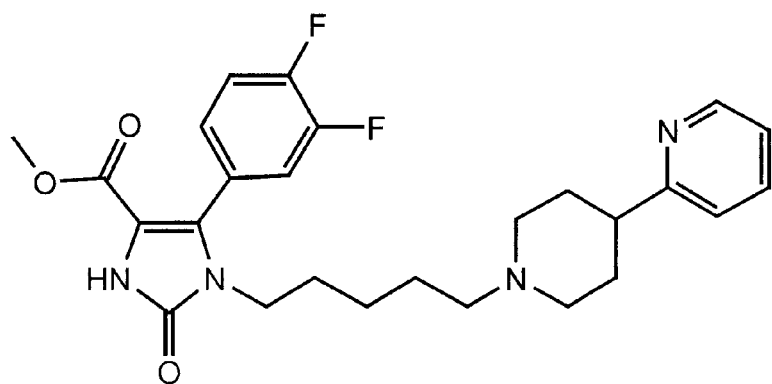
Figure 1C:
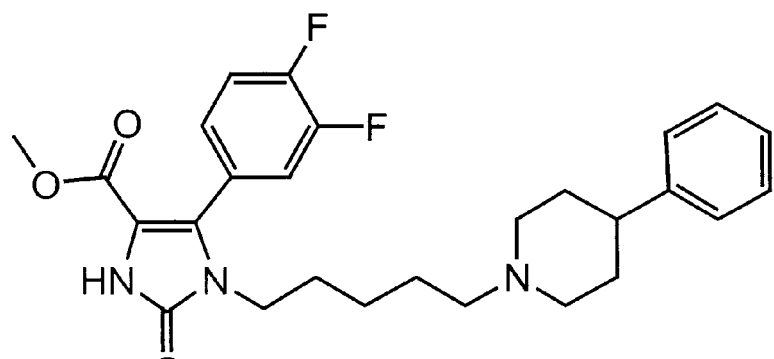
Figure 1D:
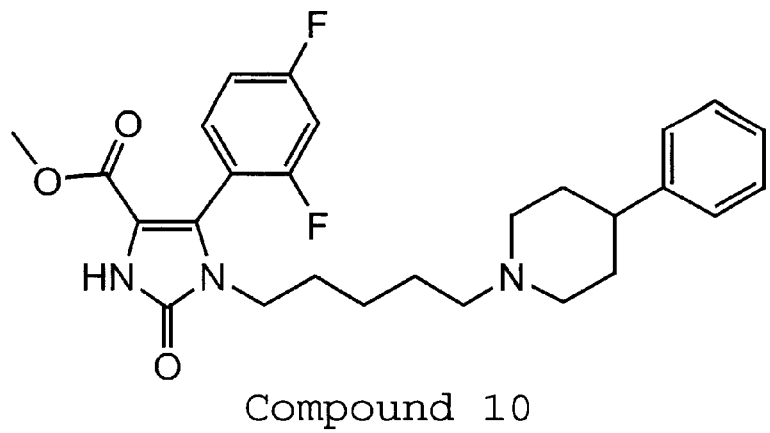
Figure 1D:
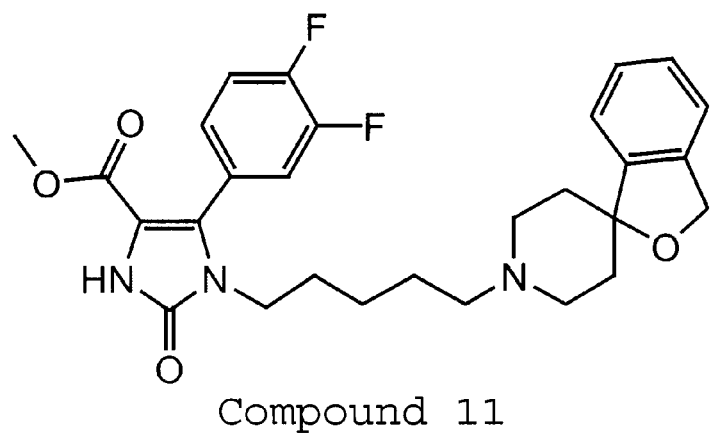
Figure 1D:
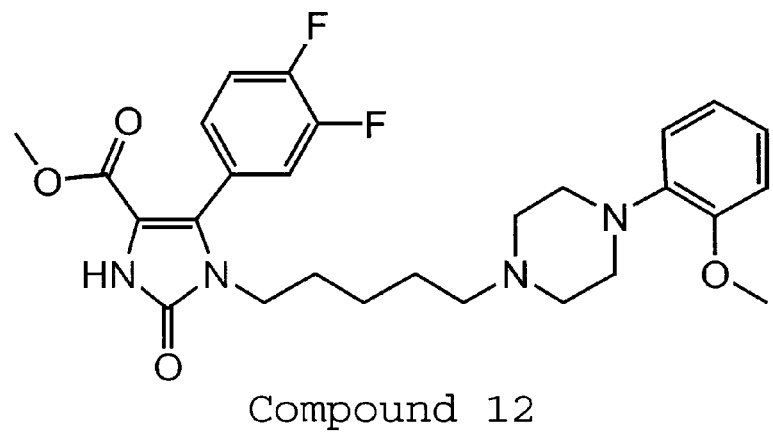
Figure 1E:
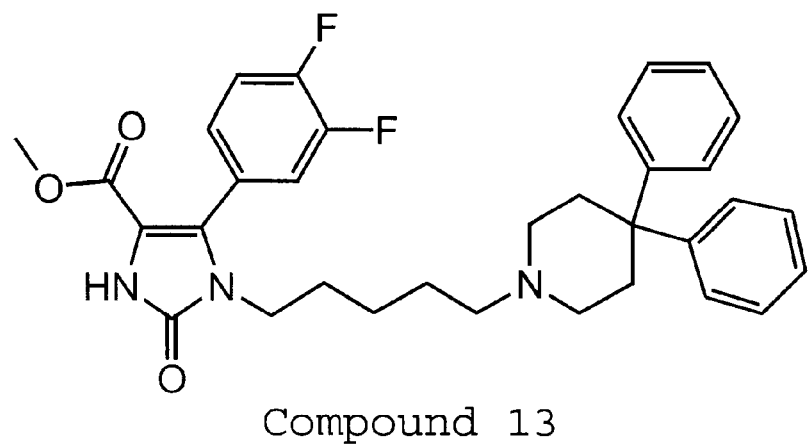
Figure 1E:
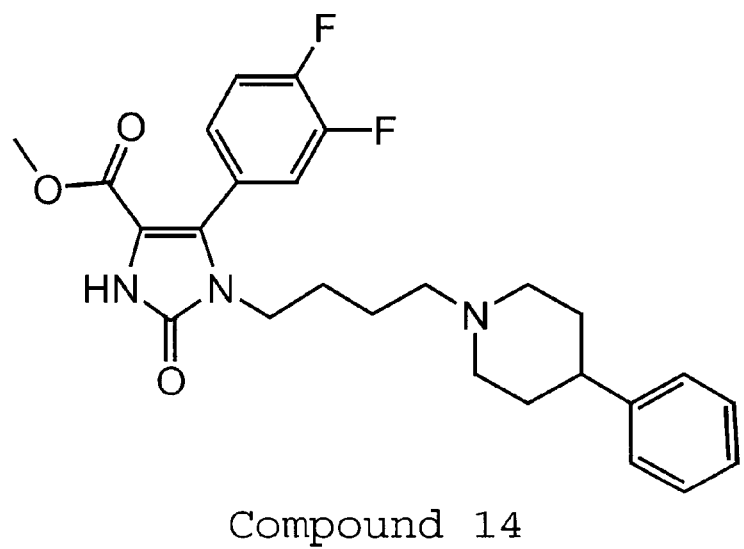
Figure 1E:
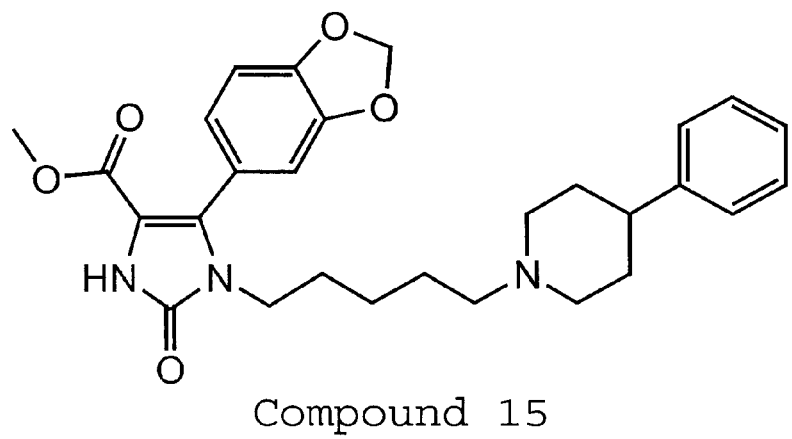
Figure 1F:
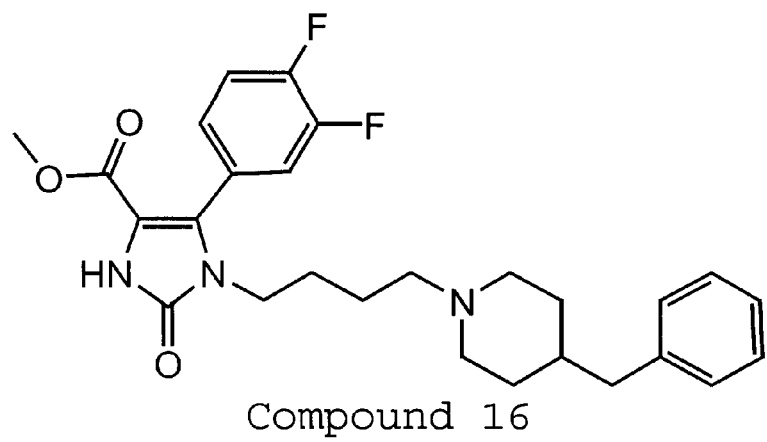
Figure 1F:
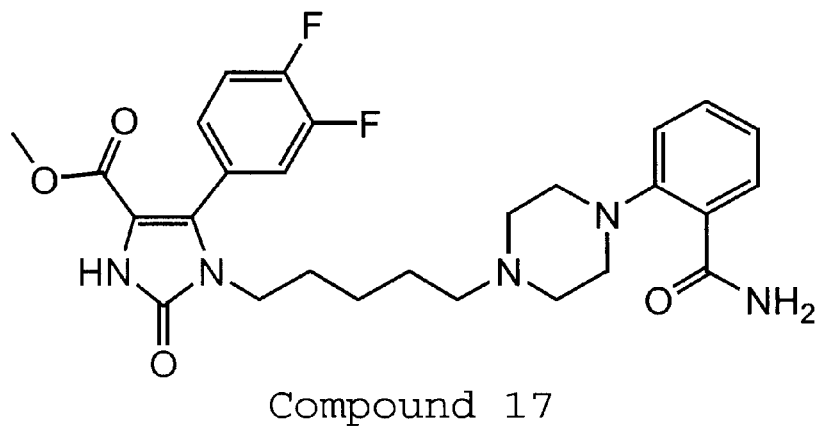
Figure 1F:
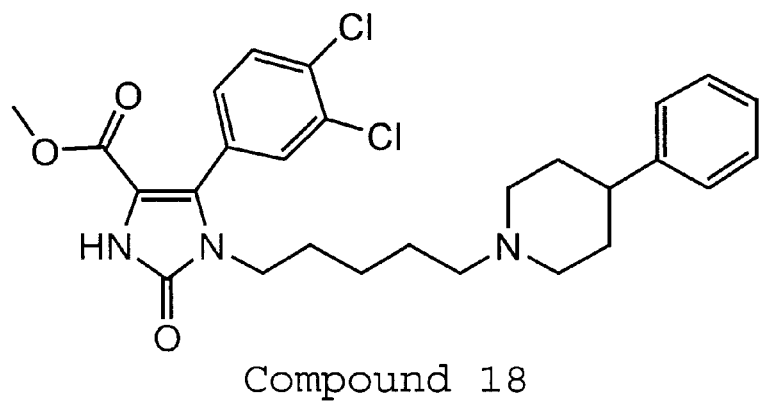
Figure 1G:
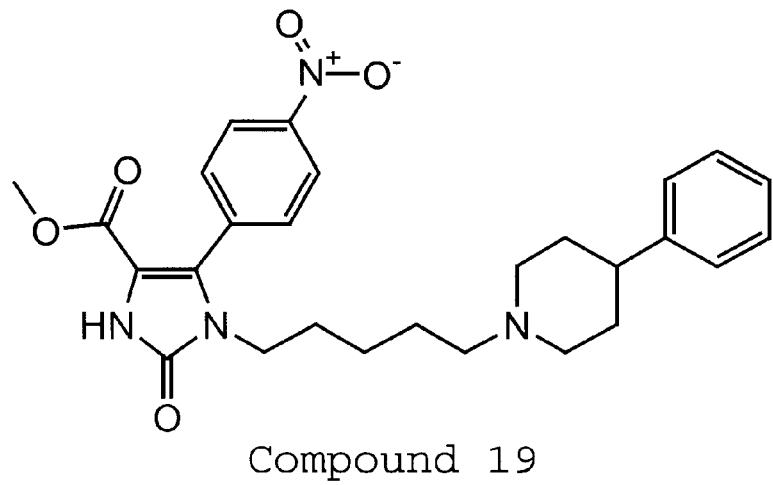
Figure 1G:
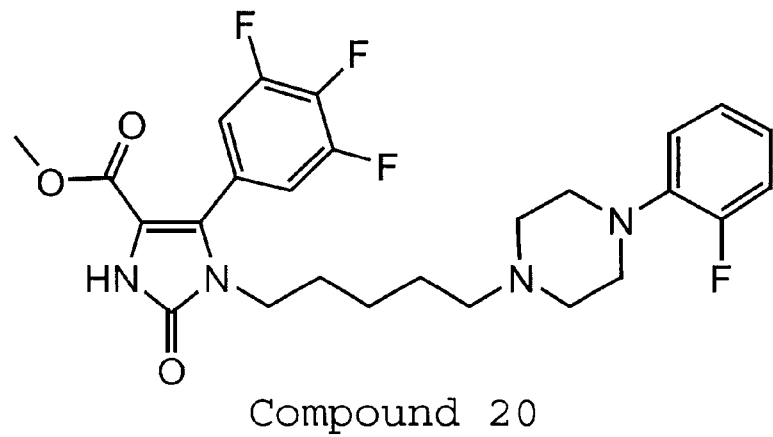
Figure 1G:
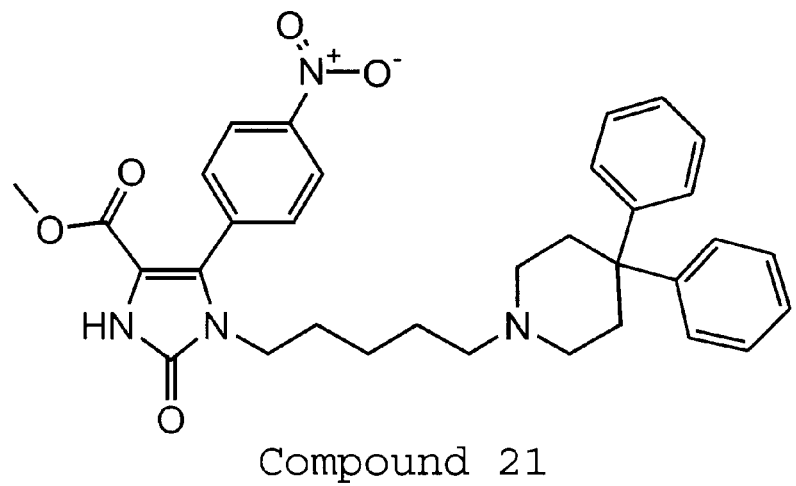
Figure 1H:
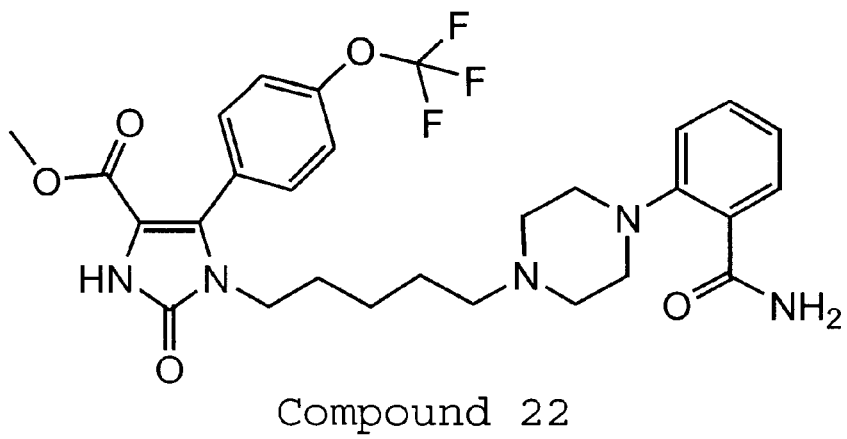
Figure 1H:
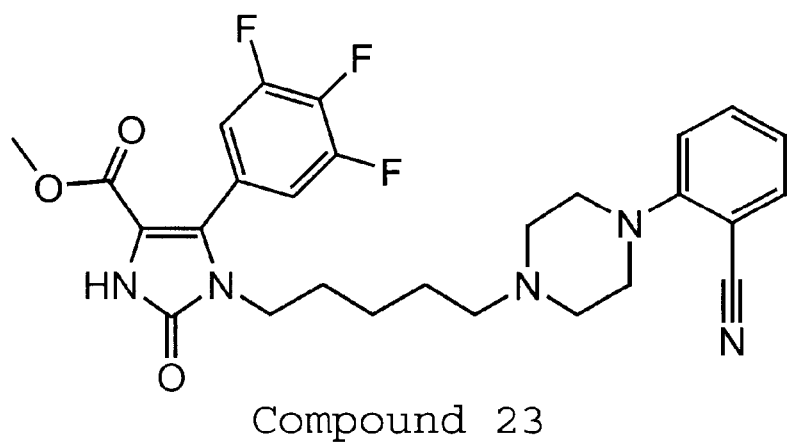
Figure 1H:
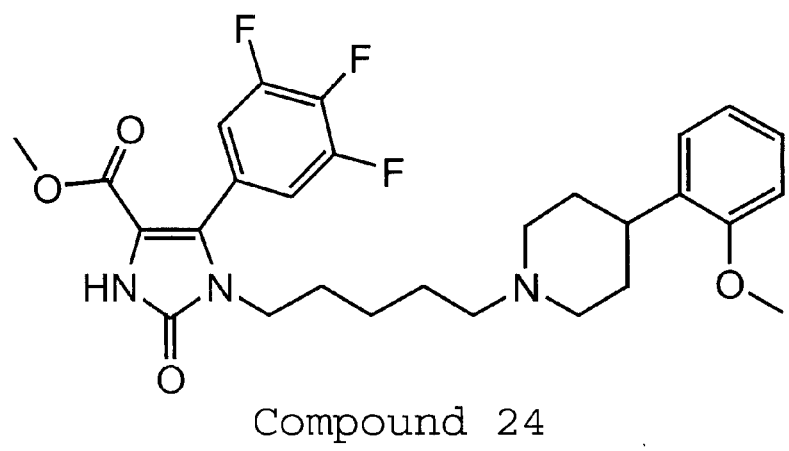
Figure 1I:
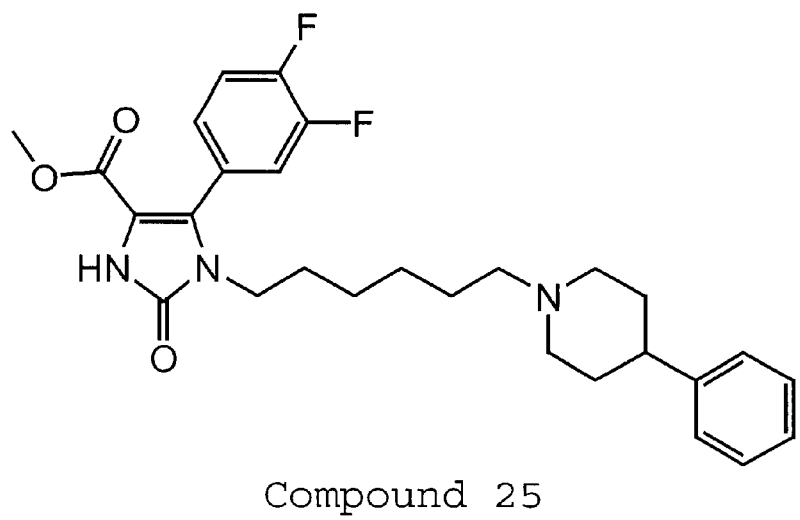
Figure 1I:
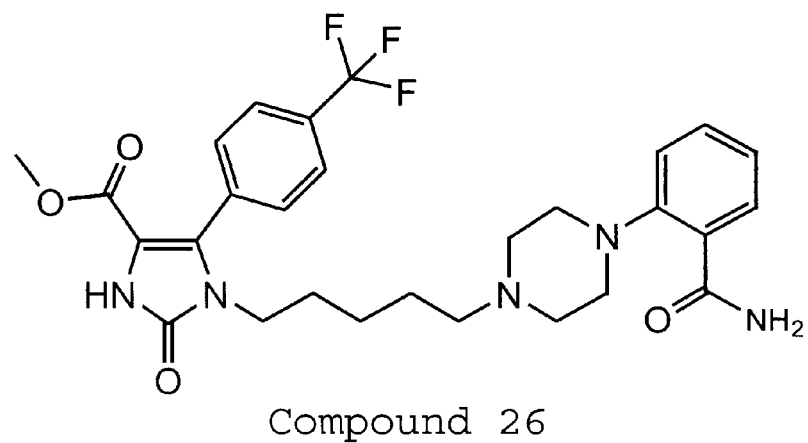
Figure 1I:
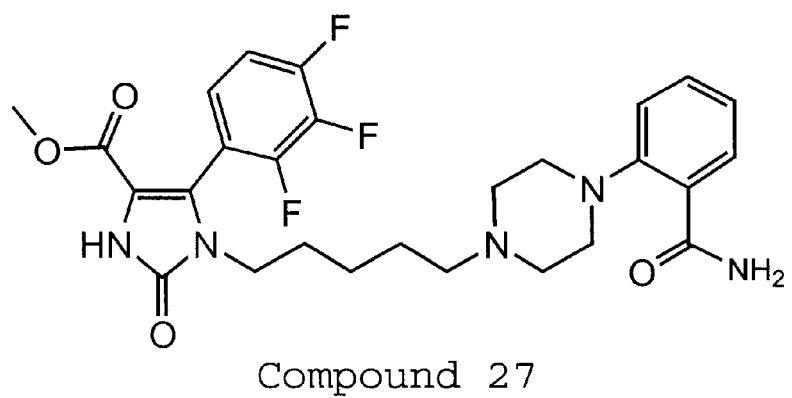
Figure 1J:
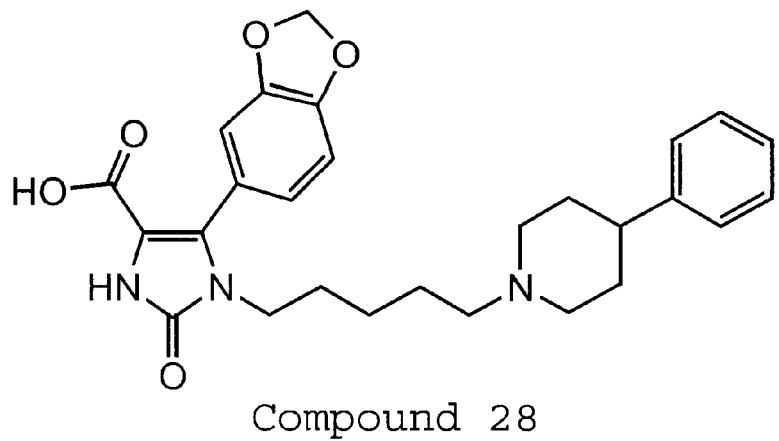
Figure 1J:
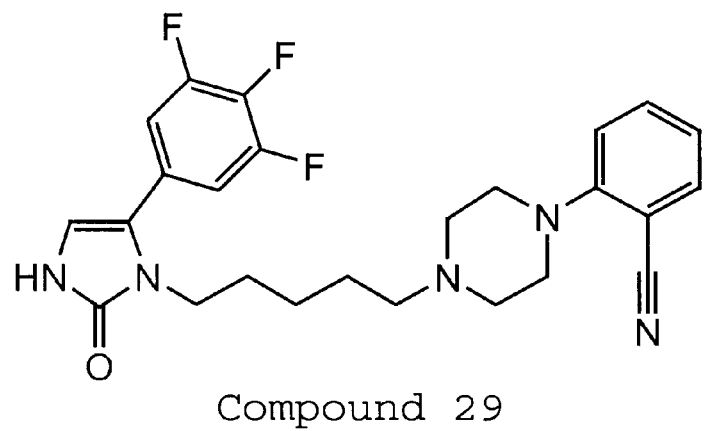
Figure 1J:
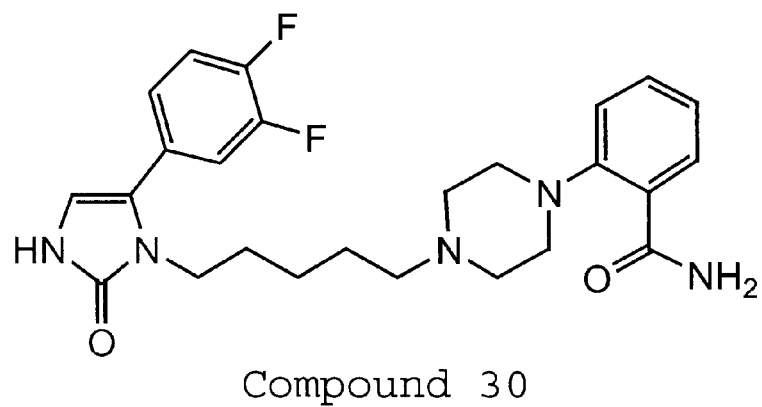
Figure 1K:
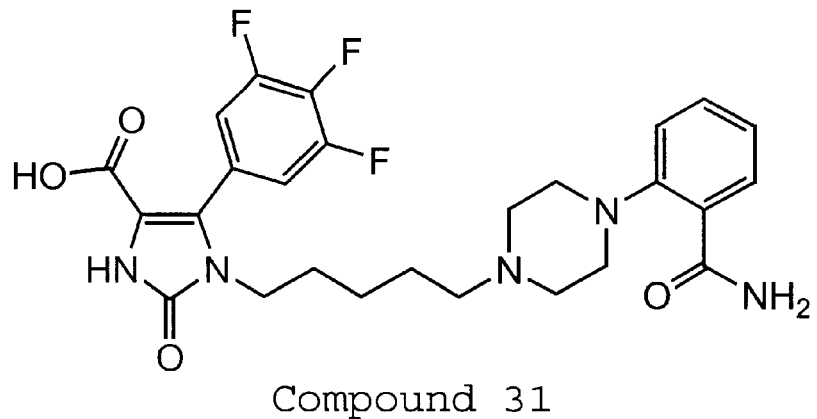
Figure 1K:
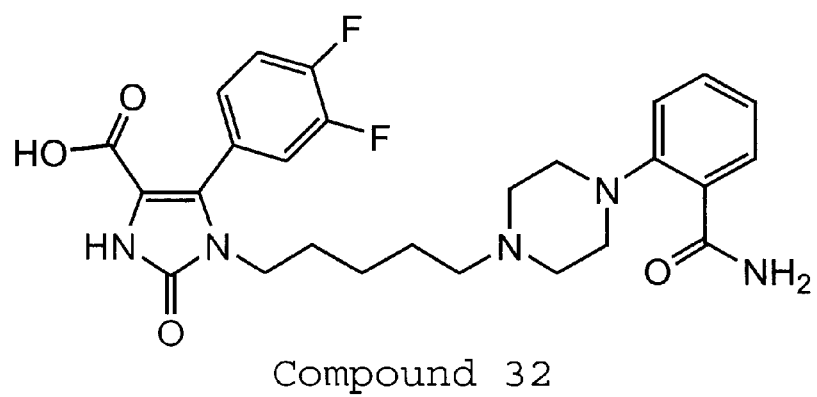
Figure 1K:
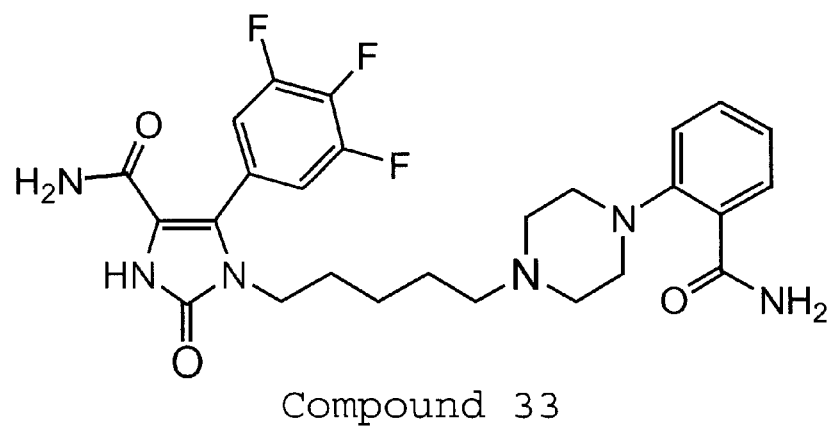
Figure 1L:
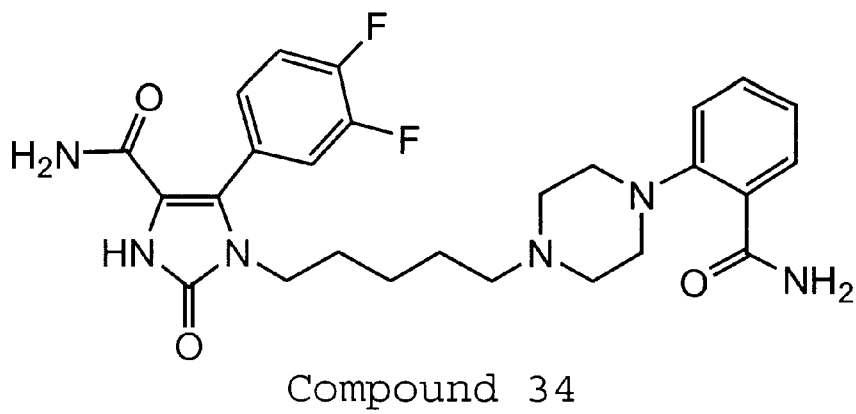
Figure 1L:
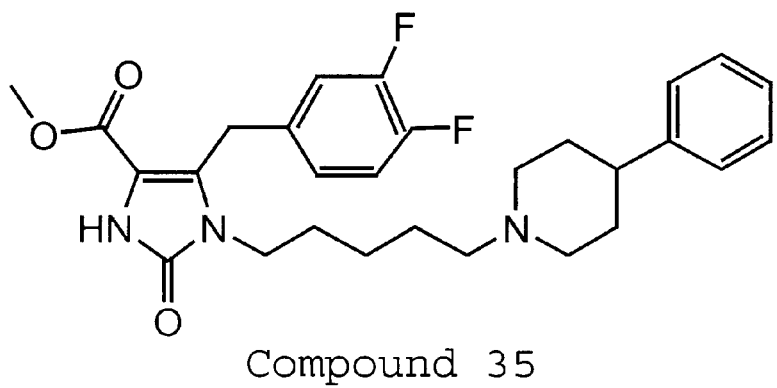
Figure 1L:
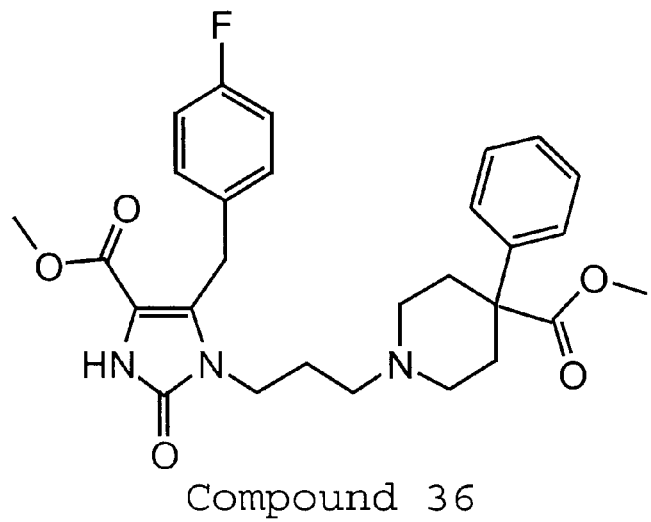
Figure 1M:
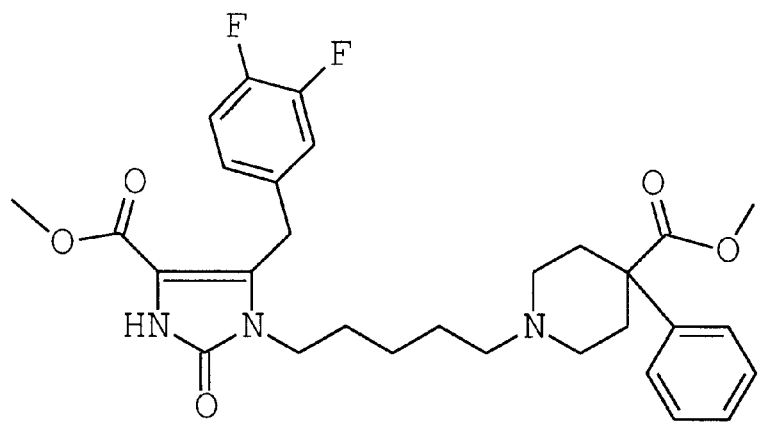
Figure 1M:
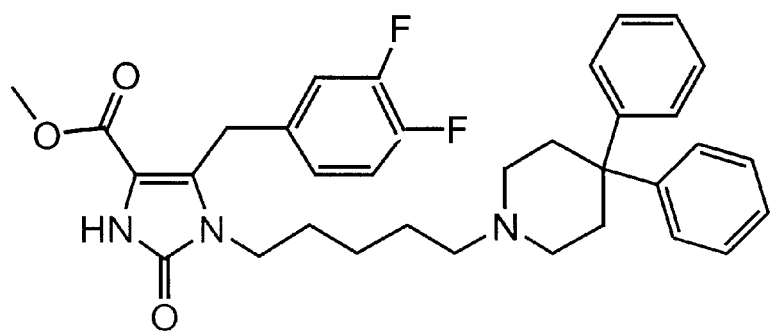
Figure 1M:
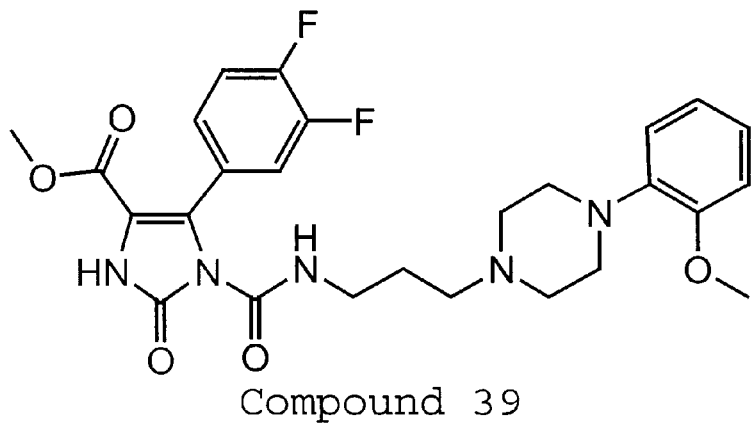
Figure 1N:
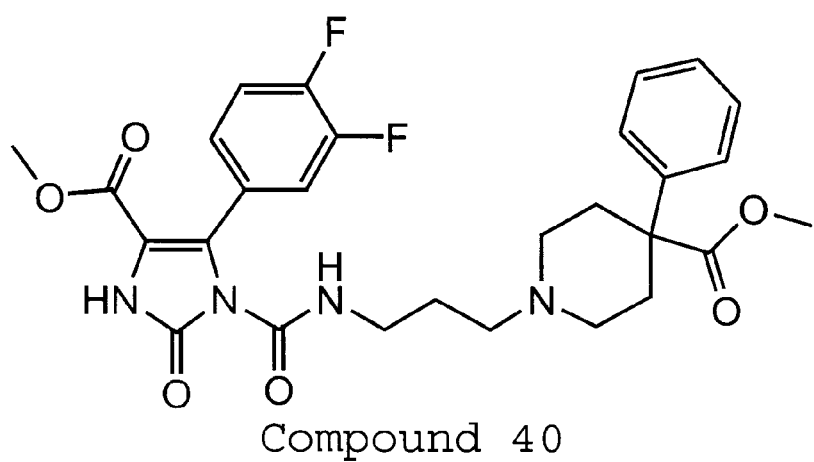

This invention provides for a compound having the structure:

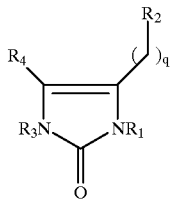

where $R_2$ is aryl or heteroaryl; wherein the aryl or heteroaryl may be substituted with one or more of F; Cl; Br; I; —CN; —$NO_2$; —$N(R_8)_2$; —$SO_2R_8$; —$SO_2N(R_8)_2$; —$(CH_2)_nC(Y)R_8$; —$(CH_2)_nYR_8$; —$(CH_2)_nC(Y)N(R_8)_2$; —$(CH_2)_nCO_2R_8$; methylenedioxy; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl;

where $R_3$ is independently H; straight chained or branched $C_1$–$C_7$ alkyl, alkoxyalkyl, monofluoroalkyl, or polyfluoroalkyl;

where $R_4$ is H, —$(CH_2)_tYR_8$, —$(CH_2)_tC(Y)N(R_8)_2$, —$(CH_2)_tC(Y)R_8$, —$(CH_2)_tCO_2R_8$, —$(CH_2)_tN(R_8)_2$, —$(CH_2)_tCN$, —$C(Y)R_8$, —$C(Y)N(R_8)_2$, —$CO_2R_8$, straight chained or branched $C_1$–$C_7$ alkyl, straight chained or branched $C_2$–$C_7$ alkenyl or alkynyl, $C_3$–$C_7$ cycloalkyl, $C_5$–$C_7$ cycloalkenyl, or phenyl or benzyl; wherein the phenyl or benzyl may be substituted with one or more of F; Cl; Br; I; —CN; —$NO_2$; —$N(R_8)_2$; —$SO_2R_8$; —$SO_2N(R_8)_2$; —$(CH_2)_nC(Y)R_8$; —$(CH_2)_nYR_8$; —$(CH_2)_nC(Y)N(R_8)_2$; —$(CH_2)_nCO_2R_8$; methylenedioxy; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl;

where each $R_8$ is independently H, straight chained or branched $C_1$–$C_7$ alkyl, straight chained or branched $C_2$–$C_7$ alkenyl or alkynyl, $C_3$–$C_7$ cycloalkyl, $C_5$–$C_7$ cycloalkenyl, or polyfluoroalkyl;

where q is an integer from 0 to 4 inclusive;

where each n independently is an integer from 0 to 7 inclusive;

where each t independently is an integer from 1 to 4 inclusive;

where each Y is independently O or S;

where $R_1$ is

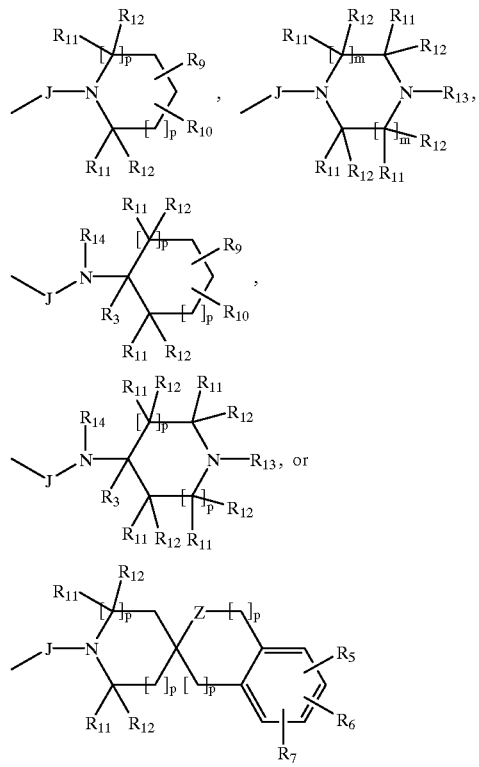

wherein $R_5$, $R_6$, and $R_7$ independently are H; F; Cl; Br; I; —CN; —$NO_2$; —$N(R_8)_2$; —$SO_2R_8$; —$(CH_2)_nC(Y)R_8$; —$(CH_2)_nYR_8$; —$(CH_2)_nC(Y)N(R_8)_2$, —$(CH_2)_nCO_2R_8$; —$SO_2N(R_8)_2$; methylenedioxy; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl;

wherein each $R_9$ is H; straight chained or branched $C_1$–$C_7$ alkyl, hydroxyalkyl, aminoalkyl, alkoxyalkyl, monofluoroalkyl, or polyfluoroalkyl; straight chained or branched $C_2$–$C_7$ alkenyl or alkynyl; $C_3$–$C_7$ cycloalkyl, monofluorocycloalkyl, or polyfluorocycloalkyl; $C_5$–$C_7$ cycloalkenyl; or aryl or heteroaryl; wherein the aryl or heteroaryl may be substituted with one or more of F; Cl; Br; I; —(CH$_2$)$_n$YR$_8$; —(CH$_2$)$_n$C(Y)R$_8$; —(CH$_2$)$_n$C(Y)N(R$_8$)$_2$; —(CH$_2$)$_n$CO$_2$R$_8$; —CN; —NO$_2$; —N(R$_8$)$_2$; —SO$_2$R$_8$; —SO$_2$N(R$_8$)$_2$; methylenedioxy; straight chained or branched C$_1$–C$_7$ alkyl, monofluoroalkyl, or polyfluoroalkyl; straight chained or branched C$_2$–C$_7$ alkenyl or alkynyl; C$_3$–C$_7$ cycloalkyl, monofluorocycloalkyl, or polyfluorocycloalkyl; or C$_5$–C$_7$ cycloalkenyl;

wherein each R$_{10}$ is H; F; —OH; —(CH$_2$)$_n$C(Y)R$_8$; —(CH$_2$)$_n$YR$_8$; —(CH$_2$)$_n$C(Y)N(R$_8$)$_2$; —(CH$_2$)$_n$CO$_2$R$_8$; —CN; —NO$_2$; —N(R$_8$)$_2$; aryl or heteroaryl; straight chained or branched C$_1$–C$_7$ alkyl, hydroxyalkyl, aminoalkyl, carboxamidoalkyl, alkoxyalkyl, monofluoroalkyl, or polyfluoroalkyl; straight chained or branched C$_2$–C$_7$ alkenyl or alkynyl; C$_3$–C$_7$ cycloalkyl, monofluorocycloalkyl, or polyfluorocycloalkyl; or C$_5$–C$_7$ cycloalkenyl; wherein the alkyl, hydroxyalkyl, alkoxyalkyl, aminoalkyl, carboxamidoalkyl, alkenyl, alkynyl, cycloalkyl or cycloalkenyl may be substituted with one or more aryl or heteroaryl; wherein the aryl or heteroaryl may be substituted with one or more of F; Cl; Br; I; —(CH$_2$)$_n$YR$_8$; —(CH$_2$)$_n$C(Y)R$_8$; —(CH$_2$)$_n$C(Y)N(R$_8$)$_2$; —(CH$_2$)$_n$CO$_2$R$_8$; —CN; —NO$_2$; —N(R$_8$)$_2$; —SO$_2$R$_8$; —SO$_2$N(R$_8$)$_2$; methylenedioxy; straight chained or branched C$_1$–C$_7$ alkyl, monofluoroalkyl, or polyfluoroalkyl; straight chained or branched C$_2$–C$_7$ alkenyl or alkynyl; C$_3$–C$_7$ cycloalkyl, monofluorocycloalkyl, or polyfluorocycloalkyl; or C$_5$–C$_7$ cycloalkenyl;

wherein each R$_{11}$ is independently H, —(CH$_2$)$_t$YR$_8$, —(CH$_2$)$_t$C(Y)N(R$_8$)$_2$, —(CH$_2$)$_t$C(Y)R$_8$, —(CH$_2$)$_t$CO$_2$R$_8$, —(CH$_2$)$_t$N(R$_8$)$_2$, —(CH$_2$)$_t$CN, —C(Y)R$_8$, —C(Y)N(R$_8$)$_2$, —CO$_2$R$_8$, straight chained or branched C$_1$–C$_7$ alkyl, straight chained or branched C$_2$–C$_7$ alkenyl or alkynyl, C$_3$–C$_7$ cycloalkyl, or C$_5$–C$_7$ cycloalkenyl;

wherein each R$_{12}$ is independently H, —(CH$_2$)$_t$YR$_8$, —(CH$_2$)$_t$C(Y)N(R$_8$)$_2$, —(CH$_2$)$_t$C(Y)R$_8$, —(CH$_2$)$_t$CO$_2$R$_8$, —(CH$_2$)$_t$N(R$_8$)$_2$, —(CH$_2$)$_t$CN, straight chained or branched C$_1$–C$_7$ alkyl, straight chained or branched C$_2$–C$_7$ alkenyl or alkynyl, C$_3$–C$_7$ cycloalkyl, or C$_5$–C$_7$ cycloalkenyl;

wherein R$_{13}$ is H, C$_1$–C$_7$ alkyl, —C(O)R$_2$, aryl or heteroaryl, C$_1$–C$_7$ alkyl substituted with one or two aryl, or C$_1$–C$_7$ alkyl substituted with one or two heteroaryl; wherein the aryl or heteroaryl may be substituted with one or more of F; Cl; Br; I; —CN; —NO$_2$; —N(R$_8$)$_2$; —SO$_2$R$_8$; —SO$_2$N(R$_8$)$_2$, —(CH$_2$)$_n$C(Y)R$_8$; —(CH$_2$)$_n$YR$_8$; —(CH$_2$)$_n$C(Y)N(R$_8$)$_2$; —(CH$_2$)$_n$CO$_2$R$_8$; methylenedioxy; straight chained or branched C$_1$–C$_7$ alkyl, monofluoroalkyl, polyfluoroalkyl, or carboxamidoalkyl; straight chained or branched C$_2$–C$_7$ aminoalkyl, alkenyl, or alkynyl; C$_3$–C$_7$ cycloalkyl; or C$_5$–C$_7$ cycloalkenyl;

wherein R$_{14}$ is H, straight chained or branched C$_1$–C$_7$ alkyl;

wherein Z is O, S, NR$_{14}$, CO, CH$_2$,

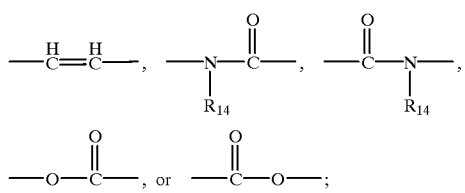

wherein each m is independently 1 or 2;
wherein each p is independently an integer from 0 to 2 inclusive;
wherein J is

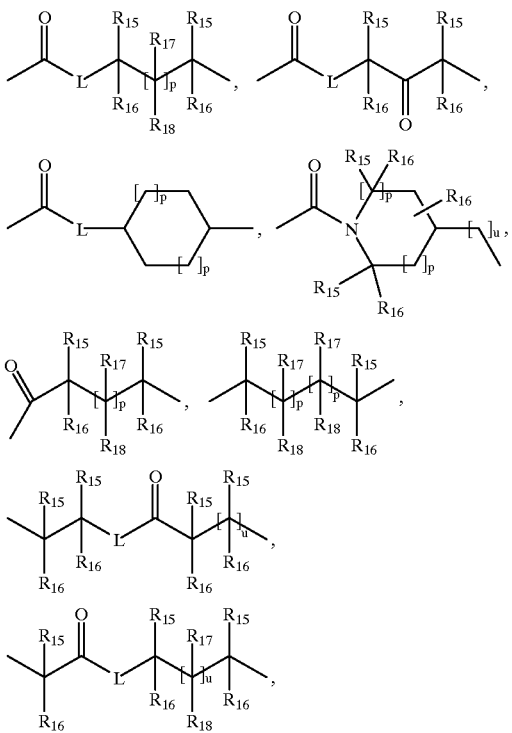

or C$_2$–C$_7$ alkenyl;

wherein each R$_{15}$ is independently H, —(CH$_2$)$_t$YR$_8$, —(CH$_2$)$_t$C(Y)N(R$_8$)$_2$, —(CH$_2$)$_t$C(Y)R$_8$, —(CH$_2$)$_t$CO$_2$R$_8$, —(CH$_2$)$_t$N(R$_8$)$_2$, —(CH$_2$)$_t$CN, —C(Y)R$_8$, —C(Y)N(R$_8$)$_2$, —CO$_2$R$_8$, straight chained or branched C$_1$–C$_7$ alkyl, straight chained or branched C$_2$–C$_7$ alkenyl or alkynyl, C$_3$–C$_7$ cycloalkyl, or C$_5$–C$_7$ cycloalkenyl;

wherein each R$_{16}$ is independently H, —(CH$_2$)$_t$YR$_8$, —(CH$_2$)$_t$C(Y)N(R$_8$)$_2$, —(CH$_2$)$_t$C(Y)R$_8$, —(CH$_2$)$_t$CO$_2$R$_8$, —(CH$_2$)$_t$N(R$_8$)$_2$, —(CH$_2$)$_t$CN, straight chained or branched C$_1$–C$_7$ alkyl, straight chained or branched C$_2$–C$_7$ alkenyl or alkynyl, C$_3$–C$_7$ cycloalkyl, or C$_5$–C$_7$ cycloalkenyl;

wherein each R$_{17}$ is independently H; F; —(CH$_2$)$_t$YR$_8$; —(CH$_2$)$_t$C(Y)N(R$_8$)$_2$; —(CH$_2$)$_t$C(Y)R$_8$; —(CH$_2$)$_t$CO$_2$R$_8$; —(CH$_2$)$_t$N(R$_8$)$_2$; —(CH$_2$)$_t$CN; —C(Y)R$_8$; —C(Y)N(R$_8$)$_2$; —CO$_2$R$_8$; straight chained or branched C$_1$–C$_7$ alkyl, monofluoroalkyl, polyfluoroalkyl, aminoalkyl, or carboxamidoalkyl; straight chained or branched C$_2$–C$_7$ alkenyl or alkynyl; C$_3$–C$_7$ cycloalkyl; or C$_5$–C$_7$ cycloalkenyl;

wherein each R$_{18}$ is independently H; F; —(CH$_2$)$_t$YR$_8$; —(CH$_2$)$_t$C(Y)N(R$_8$)$_2$; —(CH$_2$)$_t$C(Y)R$_8$; —(CH$_2$)$_t$CO$_2$R$_8$; —(CH$_2$)$_t$N(R$_8$)$_2$; —(CH$_2$)$_t$CN; straight chained or branched C$_1$–C$_7$ alkyl, monofluoroalkyl, polyfluoroalkyl, aminoalkyl, or carboxamidoalkyl; straight chained or branched C$_2$–C$_7$ alkenyl or alkynyl; C$_3$–C$_7$ cycloalkyl; or C$_5$–C$_7$ cycloalkenyl;

wherein L is S, O, or N(R$_8$);
wherein u is an integer from 0 to 1 inclusive;
or a pharmaceutically acceptable salt thereof.

The invention also provides for the (–) and (+) enantiomers of all compounds of the subject application described herein.

The invention further provides for the cis and trans isomers of all of the compounds of the subject application described herein. It is noted herein that the terms "cis" and "trans" correspond to geometric isomerism or to absolute or relative stereochemistry, as determined, for example, by NOE (Nuclear Overhauser Effect) experiments.

The compounds of the present invention are preferably at least 80% pure, more preferably at least 90% pure, and most preferably at least 95% pure.

In the present invention, the term "aryl" is used to include phenyl, benzyl, benzoyl, or naphthyl; and the term "heteroaryl" is used to include pyrazinyl, pyrrolyl, furanyl, thiophenyl, pyridyl, imidazolyl, indolyl, isoquinolyl, pyrimidinyl, triazinyl, oxazolyl, thiazolyl, benzimidazolyl, benzfurazanyl, benzofuranyl, or quinolyl.

The compounds of this invention exhibit greater affinity, preferably at least ten-fold greater affinity, for the human $\alpha_{1a}$ receptor over the human $\alpha_{1b}$ or human $\alpha_{1d}$ receptors.

In one embodiment, the compound has the structure:

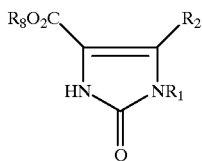

where $R_2$ is phenyl substituted with one or more of F; Cl; Br; I; —CN; —NO$_2$; —N(R$_8$)$_2$; —SO$_2$R$_8$; —SO$_2$N(R$_8$)$_2$; —(CH$_2$)$_n$C(Y)R$_8$; —(CH$_2$)$_n$YR$_8$; —(CH$_2$)$_n$C(Y)N(R$_8$)$_2$; —(CH$_2$)$_n$CO$_2$R$_8$; methylenedioxy; straight chained or branched C$_1$–C$_7$ alkyl, monofluoroalkyl, polyfluoroalkyl, aminoalkyl, or carboxamidoalkyl; straight chained or branched C$_2$–C$_7$ alkenyl or alkynyl; C$_3$–C$_7$ cycloalkyl; or C$_5$–C$_7$ cycloalkenyl; and $R_1$ is

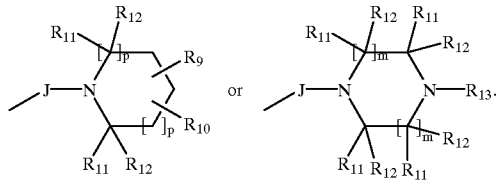

In another embodiment $R_1$ is

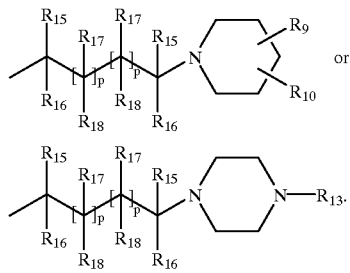

In another embodiment $R_9$ is phenyl or phenyl substituted with F; Cl; Br; I; —(CH$_2$)$_n$YR$_8$; —(CH$_2$)$_n$C(Y)R$_8$; —(CH$_2$)$_n$C(Y)N(R$_8$)$_2$; —(CH$_2$)$_n$CO$_2$R$_8$; —CN; —NO$_2$; —N(R$_8$)$_2$; —SO$_2$R$_8$; —SO$_2$N(R$_8$)$_2$; methylenedioxy; straight chained or branched C$_1$–C$_7$ alkyl, monofluoroalkyl, or polyfluoroalkyl; straight chained or branched C$_2$–C$_7$ alkenyl or alkynyl; C$_3$–C$_7$ cycloalkyl, monofluorocycloalkyl, or polyfluorocycloalkyl; or C$_5$–C$_7$ cycloalkenyl.

Preferred embodiments include a compound from the group consisting of:

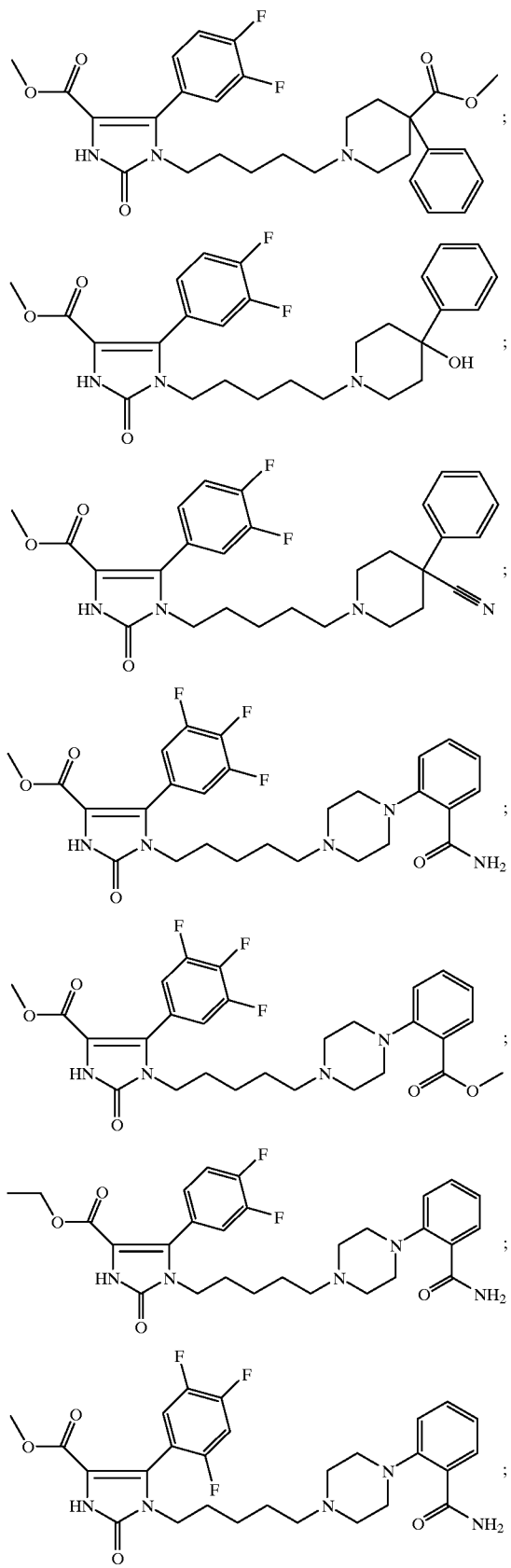

and

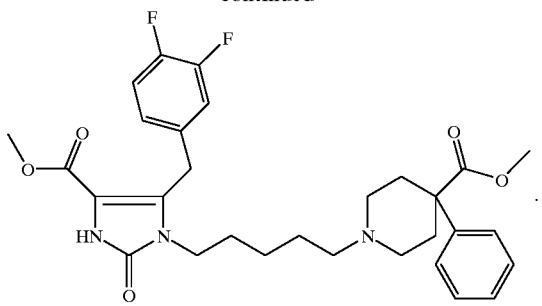

The invention provides for a pharmaceutical composition comprising a therapeutically effective amount of any of the compounds described above and a pharmaceutically acceptable carrier. In the subject invention, a "therapeutically effective amount" is any amount of a compound which, when administered to a subject suffering from a disease against which the compounds are effective, causes reduction, remission, or regression of the disease.

In one embodiment, the therapeutically effective amount is an amount from about 0.01 mg per subject per day to about 800 mg per subject per day, preferably from about 0.01 mg per subject per day to about 500 mg per subject per day, more preferably from about 0.01 mg per subject per day to about 250 mg per subject per day, more preferably from about 0.1 mg per subject per day to about 60 mg per subject per day and most preferably from about 1 mg per subject per day to about 20 mg per subject per day. In the practice of this invention, the "pharmaceutically acceptable carrier" is any physiological carrier known to those of ordinary skill in the art useful in formulating pharmaceutical compositions.

In one embodiment the pharmaceutical carrier may be a liquid and the pharmaceutical composition would be in the form of a solution. In another embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes, and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The compound can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

In another embodiment, any one of the compounds described herein additionally does not cause a fall in blood pressure at dosages effective to alleviate benign prostatic hyperplasia.

The invention provides a method of treating a subject suffering from benign prostatic hyperplasia, which comprises administering to the subject any one of the compounds described herein effective to treat benign prostatic hyperplasia. In a preferred embodiment, the compound of the pharmaceutical composition additionally does not cause a fall in blood pressure at dosages effective to alleviate benign prostatic hyperplasia. In a preferred embodiment, the compound effects treatment of benign prostatic hyperplasia by relaxing lower urinary tract tissue and in particular where lower urinary tract tissue is prostatic smooth muscle.

In the practice of this invention, the term "lower urinary tract tissue" is used to include prostatic capsule, prostate urethra, urethral smooth muscle, prostatic smooth muscle, and bladderneck.

The invention further provides a method of treating a subject suffering from elevated intraocular pressure, which comprises administering to the subject one of the compounds described herein effective to lower intraocular pressure.

The invention further provides a method of treating a subject suffering from a disorder associated with elevated blood cholesterol, which comprises administering to the subject one of the compounds described herein effective to inhibit cholesterol synthesis.

The invention provides a method of treating a subject suffering from cardiac arrhythmia, which comprises administering to the subject one of the compounds described herein effective to treat cardiac arrhythmia.

The invention further provides a method of treating a subject suffering from impotency, which comprises administering to the subject one of the compounds described herein effective to treat impotency.

The invention further provides a method of treating a subject suffering from sympathetically mediated pain, which comprises administering to the subject one of the compounds described herein effective to treat sympathetically mediated pain.

This invention provides a method of treating a subject suffering from migraine which comprises administering to the subject one of the compounds described herein effective to treat migraine.

The invention also provides a method of treating a disease which is susceptible to treatment by antagonism of the $\alpha_{1a}$ receptor, which comprises administering to the subject one of the compounds described herein effective to treat the disease.

The invention provides a method of treating a subject suffering from benign prostatic hyperplasia, which comprises administering to the subject one of the compounds described herein in combination with a 5-alpha reductase inhibitor effective to treat benign prostatic hyperplasia. In one preferred embodiment the 5-alpha reductase inhibitor is finasteride.

This invention provides for a pharmaceutical composition comprising a therapeutically effective amount of any one of the compound described herein in combination with a therapeutically effective amount of finasteride and a pharmaceutically acceptable carrier. This invention also provides for a pharmaceutical composition comprising any one of the compounds described herein present in an amount from about 0.01 mg to about 800 mg and the therapeutically effective amount of the finasteride is about 5 mg. In one embodiment, the pharmaceutical composition is any one of the compounds described herein present in an amount from about 0.1 mg to about 60 mg and the therapeutically effective amount of finasteride is about 5 mg. In another embodiment, the pharmaceutical composition is any one of the compounds described herein present in an amount from about 1 mg to about 20 mg and the therapeutically effective amount of finasteride is about 5 mg.

The invention further provides a method of relaxing lower urinary tract tissue which comprises contacting the lower urinary tract tissue with an amount of one of the compounds described herein effective to relax lower urinary tract tissue. In one embodiment the lower urinary tract tissue is prostatic smooth muscle. In one preferred embodiment, the compound additionally does not cause a fall in blood pressure when it is effective to relax lower urinary tract tissue.

The invention provides a method of relaxing lower urinary tract tissue in a subject which comprises administering to the subject an amount of one of the compounds described herein effective to relax lower urinary tract tissue. In one embodiment the lower urinary tract tissue is prostatic smooth muscle. In one preferred embodiment, the compound additionally does not cause a fall in blood pressure when it is effective to relax lower urinary tract tissue.

This invention provides for a pharmaceutical composition made by combining a therapeutically effective amount of any one of the compounds described herein and a pharmaceutically acceptable carrier.

This invention provides for a pharmaceutical composition made by combining a therapeutically effective amount of any one of the compounds described herein with a therapeutically effective amount of finasteride and a pharmaceutically acceptable carrier.

This invention provides for a process for making a pharmaceutical composition comprising combining a therapeutically effective amount of any one of the compounds described herein and a pharmaceutically acceptable carrier.

This invention provides for a process for making a pharmaceutical composition comprising combining a therapeutically effective amount of any one of the compounds described herein with a therapeutically effective amount of finasteride and a pharmaceutically acceptable carrier.

Included in this invention are pharmaceutically acceptable salts and complexes of all of the compounds described herein. The salts include but are not limited to the following acids and bases: inorganic acids which include hydrochloric acid, hydrobromic acid, hydroiodic acid, sulfuric acid, and boric acid; organic acids which include acetic acid, oxalic acid, malonic acid, succinic acid, fumaric acid, tartaric acid, maleic acid, citric acid, methanesulfonic acid, benzoic acid, glycolic acid, lactic acid, and mandelic acid; inorganic bases which include ammonia; and organic bases which include methylamine, ethylamine, hydroxyethylamine, propylamine, dimethylamine, diethylamine, trimethylamine, triethylamine, ethylenediamine, hydroxyethylamine, morpholine, piperazine, and guanidine. This invention further provides for the hydrates and polymorphs of all of the compounds described herein.

The present invention includes within its scope prodrugs of the compounds of this inventions. In general, such prodrugs will be functional derivatives of the compounds of the invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in Design of Prodrugs, ed. H. Bundgaard, Elsevier, 1985.

The present invention further includes metabolites of the compounds of the present invention. Metabolites include active species produced upon introduction of compounds of this invention into the biological milieu.

One skilled in the art will readily appreciate that appropriate biological assays will be used to determine the therapeutic potential of the claimed compounds for treating the above noted disorders.

This invention will be better understood from the Experimental Details which follow. However, one skilled in the art will readily appreciate that the specific methods and results discussed are merely illustrative of the invention as described more fully in the claims which follow thereafter.

Experimental Details
I. Synthesis of Imidazolone Examples
Scheme 1 (Diagram below)
1. 1-(5-(4-Methoxycarbonyl-4-phenylpiperidin-1-yl)pent-1-yl)-4-methoxycarbonyl-5-(3,4-difluorophenyl)-2,3-dihydro-2(1H)-imidazolone (Compound 1).
Step A: 5-(3,4-Difluorophenyl)-4-methoxycarbonyloxazole.

To a well stirred solution of the methyl isocyanoacetate (2 g, 20.2 mmol) in THF (3 mL), triethyl amine (8.4 mL, 6.06 mmol) was added and the reaction mixture was stirred for 15 minutes. Then 3,4-difluorobenzoylchloride (2.5 mL, 20.20 mmol) was added neat over a period of five minutes and the reaction mixture was allowed to stir at room temperature for 48 hours. It was then concentrated, partitioned between ethyl acetate (50 mL) and water. The organic layer was washed with 10% NaOH solution (20 mL), dried over sodium sulfate, filtered and concentrated to yield 3.8 g (79%) of a brown solid which was recrystallized from hexanes: $^1$H-NMR (CDCl$_3$) δ3.74(s, 3H), 7.47–7.50 (m, 1 H), 7.92 (s, 2 H), 8.01–8.10 (m, 2 H).
Step B: 2-Amino-3-(3,4-difluorophenyl)-3-oxopropionic acid methyl ester.

To 5-(3,4-difluorophenyl)-4-methoxycarbonyloxazole (1.0 g, 4.18 mmol) in methanol (6 mL), 1N HCl (2 mL) was added and the mixture was heated at 50° C. for 2 hours. The reaction mixture was then concentrated to yield a syrup. Ether was added and the solution filtered to give 1.0 g (87%) of the product as a white solid: $^1$H-NMR (CDCl$_3$) 3.74 (s, 3 H), 6.15 (s, 1H), 7.45–7.55 (m, 1H), 8.11–8.13 (m, 2H)
Step C: 1-Bromo-5-isocyanatopentane.

To a solution of trimethylsilylazide (7.46 mL, 93.67 mmol) in dioxane (10 mL), 6-bromohexanoyl chloride (10 g, 46.83 mmol) was added and the solution was heated at 80° C. for 4 hours. The reaction mixture was concentrated to give a liquid. Distillation (oil bath temp. 135° C., distilling temperature 94° C.) of the liquid yielded 7 g (78%) of the product as a liquid: $^1$H-NMR (CDCl$_3$) δ1.50–1.92 (m, 6 H), 3.33 (t, J=7.0 Hz, 2H), 3.43 (t, J=7.0 Hz, 2H). IR: 2360 cm$^{-1}$.
Step D: 1-(5-Bromopent-1-yl)-5-(3,4-difluorophenyl)-2,3-dihydro-4-methoxycarbonyl-2(1H)-imidazolone.

A solution of 2-amino-3-(3,4-difluorophenyl)-3-oxopropionic acid methyl ester (0.475 g, 2.07 mmol) and 1-bromo-5-isocyanotopentane (0.7 mL, 3.73 mmol) in water (3 mL) was refluxed for four hours. The reaction mixture was partitioned between EtOAc (10 mL) and water (5 mL). The organic layer was dried, filtered and concentrated to yield 380 mg (45%) of the crude product which was used as such for the subsequent step.
Step E: 1-(5-(4-Methoxycarbonyl-4-phenylpiperidin-1-yl)pent-1-yl)-4-methoxycarbonyl-5-(3,4-difluorophenyl)-2,3-dihydro-2(1H)-imidazolone.

To a stirred solution of 1-(5-bromopent-1-yl)-5-(3,4-difluorophenyl)-2,3-dihydro-4-methoxycarbonyl-2(1H)-imidazolone (0.357 g, 0.88 mmol) in dioxane (10 mL) was added 4-methoxycarbonyl-4-phenylpiperidine (0.388 g, 1.77 mmol), potassium carbonate (0.544 g, 2.65 mmol) and sodium iodide (0. g, 1.77 mmol), and the mixture refluxed for 24 hours. The reaction mixture was cooled to room temperature, concentrated and partitioned between chloroform (40 mL) and water (5 mL). The organic layer was dried over sodium sulfate, filtered and concentrated. The crude product was purified by column chromatography (ethyl acetate: methanol, 4.4:0.6) to yield 0.235 g (48%) of the required product as a colorless oil. Hydrochloride salt (recrystallized from ether) : white solid; m.p. 180–182° C. Analysis calculated for $C_{29}H_{34}ClF_2N_3O_5 \cdot 1.7\ H_2O$: C, 57.23; H,6.19. Found: C, 57.14; H, 6.20.

The following compounds were prepared similarly.
2. 5-(3,4-Difluorophenyl)-2,3-dihydro-4-methoxycarbonyl-1-(5-(4-cyano-4-phenylpiperidin-1-yl)pent-1-yl)-2(1H)-imidazolone (Compound 2).

Hydrochloride salt (recrystallized from ether): white solid; m.p. 190–192° C. Analysis calculated for $C_{28}H_{31}ClF_2N_4O_3 \cdot 0.6\ CH_2Cl_2$: C, 57.64; H, 5.45; N, 9.40. Found: C, 57.64; H, 5.57; N, 9.30.
3. 5-(3,4-Difluorophenyl)-2,3-dihydro-4-methoxycarbonyl-1-(5-(4-hydroxy-4-phenylpiperidin-1-yl)pent-1-yl)-2(1H)-imidazolone (Compound 3).

Hydrochloride salt (recrystallized from ether): white solid; m.p. 193–195° C. Analysis calculated for $C_{27}H_{32}ClF_2N_3O_4 \cdot 0.60\ H_2O$: C, 59.31; H, 6.12; N, 7.68. Found: C, 59.44; H, 6.05; N, 7.32.
4. 1-(5-(4-(2-Aminocarbonylphenyl)piperazin-1-yl)pent-1-yl)-5-(3,4,5-trifluorophenyl)-2,3-dihydro-4-methoxycarbonyl-2(1H)-imidazolone (Compound 4).

Hydrochloride salt (recrystallized from ether): pale yellow solid; m.p. 194–196° C. Analysis calculated for $C_{27}H_{32}Cl_2F_3N_5O_4 \cdot 0.8\ CH_2Cl_2$: C, 48.64; H,4.93; N, 10.23. Found: C, 48.92; H, 4.65; N, 10.12.
5. 5-(3,4,5-Trifluorophenyl)-2,3-dihydro-4-methoxycarbonyl-1-(5-(4-(2-methoxycarbonylphenyl)piperazin-1-yl)pent-1-yl)-2(1H)-imidazolone (Compound 5).

Hydrochloride salt (recrystallized from ether): yellow solid; m.p. 185–187° C. Analysis calculated for $C_{28}H_{33}Cl_2F_3N_4O_5 \cdot 0.1H_2O$: C, 52.94; H,5.27; N, 8.82. Found: C, 52.87; H, 5.44; N, 8.43.
6. 1-(5-(4-(2-Aminocarbonylphenyl)piperazin-1-yl)pent-1-yl)-4-ethoxycarbonyl-5-(3,4-difluorophenyl)-2,3-dihydro-2(1H)-imidazolone (Compound 6).

Hydrochloride salt (recrystallized from ether): pale yellow solid; m.p. 241–243° C. Analysis calculated for $C_{28}H_{35}Cl_2F_2N_5O_4$: C, 54.79; H, 5.75; N, 11.42. Found: C, 54.97; H, 5.77; N, 11.29.
7. 1-(5-(4-(2-Aminocarbonylphenyl)piperazin-1-yl)pent-1-yl)-5-(2,4,5-trifluorophenyl)-2,3-dihydro-4-methoxylcarboxy-2(1H)-imidazolone (Compound 7).

Hydrochloride salt (recrystallized from ether): off-white solid; m.p. 224–226° C. Analysis calculated for $C_{27}H_{32}Cl_2F_3N_5O_4 \cdot 0.2CH_2Cl_2$: C, 54.54; H, 5.28; N, 11.69. Found: C, 54.4; H, 5.35; N, 11.42.
8. 5-(3,4-Difluorophenyl)-2,3-dihydro-4-methoxycarbonyl-1-(5-(4-(2-pyridyl)piperidin-1-yl)pent-1-yl)-2(1H)-imidazolone (Compound 8).

Hydrochloride salt (recrystallized from ether): hygroscopic brown solid; m.p. 178–180° C.
9. 5-(3,4-Difluorophenyl)-2,3-dihydro-4-methoxycarbonyl-1-(5-(4-phenylpiperidin-1-yl)pent-1-yl)-2(1H)-imidazolone (Compound 9).

Hydrochloride salt (recrystallized from ether): brown solid; m.p. 140–142° C. Analysis calculated for $C_{27}H_{32}ClF_2N_3O_3 \cdot 1.6H_2O$: C, 59.09; H, 6.46; N, 7.66. Found: C, 59.11; H, 6.21; N, 7.04.
10. 5-(2,4-Difluorophenyl)-2,3-dihydro-4-methoxycarbonyl-1-(5-(4-phenylpiperidin-1-yl)pent-1-yl)-2(1H)-imidazolone (Compound 10).

Hydrochloride salt (recrystallized from ether): yellow solid; m.p. 138–141° C.
11. 5-(3,4-Difluorophenyl)-2,3-dihydro-1-(5-spiro[1,3-dihydroisobenzofuran-1,4-piperidin-1-yl]pent-1-yl)-4-methoxycarbonyl-2(1H)-imidazolone (Compound 11).

Hydrochloride salt (recrystallized from ether): yellow solid; m.p. 183–185° C. Analysis calculated for $C_{28}H_{32}ClF_2N_3O_4$: C, 61.37; H, 5.89; N, 7.67. Found: C, 61.40; H 5.89; N, 7.68.

12. 5-(3,4-Difluorophenyl)-2,3-dihydro-4-methoxycarbonyl-1-(5-(4-(2-methoxylphenyl)piperazin-1-yl)pent-1-yl)-2(1H)-imidazolone (Compound 12).

Hydrochloride salt (recrystallized from ether): yellow solid; m.p. 176–178° C. Analysis calculated for $C_{27}H_{34}Cl_2F_2N_4O_4.0.5\ H_2O$: C, 54.37; H, 5.91; N, 9.39. Found: C, 54.64; H, 6.22; N, 8.98.

13. 5-(3,4-Difluorophenyl)-2,3-dihydro-4-methoxycarbonyl-1-(5-(4,4-diphenyl-piperidin-1-yl)pent-1-yl)-2(1H)-imidazolone (Compound 13).

Hydrochloride salt (recrystallized from ether): brown solid; m.p. 142–144° C. Analysis calculated for $C_{33}H_{36}ClF_2N_3O_3.2.0\ H_2O$: C, 62.70; H, 6.38; N, 6.65. Found: C, 63.03; H, 6.25; N, 6.14.

14. 5-(3,4-Difluorophenyl)-2,3-dihydro-4-methoxycarbonyl-1-(4-(4-phenylpiperidin-1-yl)but-1-yl)-2(1H)-imidazolone (Compound 14).

Hydrochloride salt (recrystallized from ether): white solid; m.p. 142–144° C.

15. 2,3-Dihydro-4-methoxycarbonyl-5-(3,4-methylenedioxyphenyl)-1-(5-(4-phenylpiperidin-1-yl)pent-1-yl)-2(1H)-imidazolone (Compound 15).

Hydrochloride salt (recrystallized from ether): white solid; m.p. 187–190° C. Analysis calculated for $C_{28}H_{34}ClN_3O_5.1.60\ H_2O$: C, 60.39; H, 6.73; N, 7.55. Found: C, 60.67; H, 6.61; N, 7.09.

16. 1-(4-(4-Benzylpiperidin-1-yl)but-1-yl)-5-(3,4-difluorophenyl)-2,3-dihydro-4-methoxycarbonyl-2(1H)-imidazolone (Compound 16).

Hydrochloride salt (recrystallized from ether): yellow solid; m.p. 152–154° C. Analysis calculated for $C_{27}H_{32}ClF_2N_3O_3.2H_2O$: C, 58.32; H, 6.53; N, 7.56. Found: C, 58.31; H, 6.24; N, 7.82.

17. 1-(5-(4-(2-Aminocarbonylphenyl)piperazin-1-yl)pent-1-yl)-5-(3,4-difluorophenyl)-2,3-dihydro-4-methoxycarbonyl-2(1H)-imidazolone (Compound 17).

Hydrochloride salt (recrystallized from ether): yellow solid; m.p. 210–211° C. Analysis calculated for $C_{27}H_{33}Cl_2F_2N_5O_4.0.8\ CH_2Cl_2$: C, 49.95; H, 5.22; N, 10.48. Found: C, 49.8; H, 5.29; N, 10.2.

18. 5-(3,4-Dichlorophenyl)-2,3-dihydro-4-methoxycarbonyl-1-(5-(4-phenylpiperidin-1-yl)pent-1-yl)-2(H)-imidazolone (Compound 18).

Hydrochloride salt (recrystallized from ether): yellow solid; m.p. 165–167° C. Analysis calculated for $C_{27}H_{32}Cl_3N_3O_3.2.6\ H_2O$: C, 54.07; H, 6.27; N, 7.01. Found: C, 54.19; H, 5.95; N, 6.66.

19. 4-Methoxycarbonyl-2,3-dihydro-5-(4-nitrophenyl)-1-(5-(4-phenylpiperidin-1-yl)pent-1-yl)-2(1H)-imidazolone (Compound 19).

Hydrochloride salt (recrystallized from ether): brown solid; m.p. 183–186° C.

20. 5-(3,4,5-Trifluorophenyl)-2,3-dihydro-1-(5-(4-(2-fluorophenyl)piperazin-1-yl)pent-1-yl)-4-methoxylcarboxy-2(1H)-imidazolone (Compound 20).

Hydrochloride salt (recrystallized from ether): white solid; m.p. 203–205° C. Analysis calculated for $C_{26}H_{29}ClF_4N_4O_3.0.3\ CH_2Cl_2$: C, 54.23; H, 5.12; N, 9.62. Found: C, 54.41; H, 5.39; N, 9.42.

21. 2,3-Dihydro-4-methoxycarbonyl-5-(4-nitrophenyl)-1-(5-(4,4-diphenylpiperidin-1-yl)pent-1-yl)-2(H)-imidazolone (Compound 21).

Hydrochloride salt (recrystallized from ether): light brown solid; m.p. 215–217° C. Analysis calculated for $C_{33}H_{37}ClN_4O_5.1.0\ EtOAc$: C, 64.11; H, 6.54; N, 8.08. Found: C, 64.28; H, 6.54; N, 8.00.

22. 1-(5-(4-(2-Aminocarbonylphenyl)piperazin-1-yl)pent-1-yl)-5-(4-trifluoromethoxyphenyl)-2,3-dihydro-4-methoxycarbonyl-2(1H)-imidazolone (Compound 22).

Hydrochloride salt (recrystallized from ether): white solid; m.p. 210–212° C.; Analysis calculated for $C_{28}H_{34}Cl_2F_3N_5O_5.0.2\ CH_2Cl_2$: C, 50.90; H, 5.21; N, 10.52. Found: C, 50.94; H, 5.20; N, 10.10.

23. 1-(5-(4-(2-Cyanophenyl)piperazin-1-yl)pent-1-yl)-5-(3,4,5-trifluorophenyl)-2,3-dihydro-4-methoxycarbonyl-2(1H)-imidazolone (Compound 23).

Hydrochloride salt (recrystallized from ether): white solid; m.p. 190–192° C. Analysis calculated for $C_{27}H_{30}Cl_2F_3N_5O_3.0.3\ CH_2Cl_2$: C, 52.38; H, 4.93; N, 11.19. Found: C, 52.63; H, 5.24; N, 10.72.

24. 5-(3,4,5-Trifluorophenyl)-2,3-dihydro-4-methoxycarbonyl-1-(5-(4-(2-methoxyphenyl)piperidin-1-yl)pent-1-yl)-2(1H)-imidazolone (Compound 24).

Hydrochloride salt (recrystallized from ether): yellow solid; m.p. 182–184° C. Analysis calculated for $C_{28}H_{33}ClF_3N_3O_4.0.3\ CH_2Cl_2$: C, 57.27; H, 5.71; N, 7.08. Found: C, 57.40; H, 5.68; N, 6.82.

25. 5-(3,4-Difluorophenyl)-2,3-dihydro-4-methoxycarbonyl-1-(6-(4-phenylpiperidin-1-yl)hex-1-yl)-2(1H)-imidazolone (Compound 25).

Hydrochloride salt (recrystallized from ether): yellow solid; m.p. 186–187° C. Analysis calculated for $C_{28}H_{34}F_2ClN_3O_3.1.50\ H_2O$: C, 59.94; H, 6.65; N, 7.49. Found: C, 59.86; H, 6.48; N, 7.59.

26. 1-(5-(4-(2-Aminocarbonylphenyl)piperazin-1-yl)pent-1-yl)-5-(4-trifluoromethylphenyl)-2,3-dihydro-4-methoxycarbonyl-2-(1H)-imidazolone (Compound 26).

Hydrochloride salt (recrystallized from ether): white solid; m.p. 198–201° C. Analysis calculated for $C_{28}H_{34}Cl_2F_3N_5O_4.1\ H_2O$: C, 51.70; H, 5.58; N, 10.77. Found: C, 51.93; H, 5.28; N, 10.43.

27. 1-(5-(4-(2-Aminocarbonylphenyl)piperazin-1-yl)pent-1-yl)-5-(2,3,4-trifluorophenyl)-2,3-dihydro-4-methoxycarbonyl-2(1H)-imidazolone (Compound 27).

Hydrochloride salt (recrystallized from ether): yellow solid; m.p. 220–222° C.; Analysis calculated for $C_{27}H_{32}Cl_2F_3N_5O_4.0.3\ CH_2Cl_2$: C, 50.92; H, 5.10; N, 10.88. Found: C, 50.92; H, 5.10; N, 10.68.

28. 4-Carboxy-2,3-dihydro-5-(3,4-methylenedioxyphenyl)-1-(5-(4-phenylpiperidin-1-yl)pent-1-yl)-2(1H)-imidazolone (Compound 28).

To a stirred solution of Compound 15 (0.033 g, 0.062 mmol) in methanol (6 mL), 1M LiOH (0.24 mL, 0.249 mmol) was added and the solution was refluxed for 24 hours. It was then concentrated, neutralized with 5% $Na_2HPO_4$ (till pH=6), extracted into EtOAc (30 mL), dried over sodium sulfate, filtered and concentrated. Purification by column chromatography (EtOAc:MeOH:methanolic $NH_3$; 4.6:0.2:0.2) yielded 0.022 g (74%) of the product as a syrup. Hydrochloride salt (recrystallized from ether): white solid; m.p. 133–135° C.

29. 1-(5-(4-(2-Cyanophenyl)piperazin-1-yl)pent-1-yl)-5-(3,4,5-trifluorophenyl)-2,3-dihydro-2(1H)-imidazolone (Compound 29).

Compound 31 (0.17 g, 0.031 mmol) in a small flask was heated at 200° C. for 24 hours. The flask was cooled to room temperature. The residue was extracted with dichloromethane (20 mL). The extract was dried over sodium sulfate, filtered and concentrated. The residue was purified by column chromatography (ethyl acetate:methanol; 4.5:0.5) to give 0.014 g (93%) a syrup. Hydrochloride salt (recrystallized from ether): brown solid; m.p. 185–187° C.; Analysis calculated for $C_{25}H_{28}Cl_2F_3N_5O.1.4EtOAc$: C, 55.20; H, 5.93; N, 10.52. Found: C, 55.48; H, 5.87; N, 10.18.

30. 1-(5-(4-(2-Aminocarbonylphenyl)piperazin-1-yl)pent-1-yl)-5-(3,4-difluorophenyl)-2,3-dihydro-2(1H)-imidazolone (Compound 30).

Compound 32 (0.022 g, 0.0425 mmol) in a small flask was heated at 200° C. for 24 hours. The flask was cooled to room temperature. The residue was extracted into dichloromethane (20 mL), dried over sodium sulfate, filtered and concentrated. After purification by column chromatography (ethylacetate: methanol; 4.5:0.5), the product (0.015 g, 75% yield) was obtained as a syrup. Hydrochloride salt (recrystallized from ether): light brown solid; m.p. 183–185° C. Analysis calculated for $C_{25}H_{31}Cl_2F_2N_5O_2$.0.70 $CH_2Cl_2$: C, 51.28; H, 5.43; N, 11.64. Found: C, 51.82; H, 5.31; N, 11.20

31. 1-(5-(4-(2-Aminocarbonylphenyl)piperazin-1-yl)pent-1-yl)-4-carboxy-5-(3,4,5-trifluorophenyl)-2,3-dihydro-2(1H)-imidazolone (Compound 31).

To a stirred solution of Compound 4 (0.079 g, 0.13 mmol) in 6 mL of methanol, 1M LiOH (0.52 mL, 0.521 mmol) was added and the solution was refluxed for 24 hours. It was then concentrated, neutralized with 5% $Na_2HPO_4$ (till pH=6), extracted into 30 mL EtOAc, dried over sodium sulfate, filtered and concentrated. Purification by column chromatography (EtOAc:MeOH:methanolic $NH_3$; 4.6:0.2:0.2) yielded 0.059 g (83%) of the product as a syrup. Hydrochloride salt (recrystallized from ether): yellow solid; m.p. 188–190° C.

32. 1-(5-(4-(2-Aminocarbonylphenyl)piperazin-1-yl)pent-1-yl)-4-carboxy-5-(3,4-difluorophenyl)-2,3-dihydro-2(1H)-imidazolone (Compound 32).

To a stirred solution of Compound 17 (0.117 g, 0.22 mmol) in 6 mL of methanol, 1M LiOH (0.887 mL, 0.887 mmol) was added and the solution was refluxed for 24 hours. It was then concentrated, neutralized with 5% $Na_2HPO_4$ to pH=6, extracted into 30 mL EtOAc, dried over sodium sulfate, filtered and concentrated. Purification by column chromatography (EtOAc:MeOH:methanolic $NH_3$; 4.6:0.2:0.2) yielded 0.126 g (98%) of the product as a syrup. Hydrochloride salt (recrystallized from ether): pale yellow solid; m.p. 193–195° C.

33. 4-Aminocarbonyl-1-(5-(4-(2-aminocarbonylphenyl)piperazin-1-yl)pent-1-yl)-5-(3,4,5-trifluorophenyl)-2,3-dihydro-2(1H)-imidazolone (Compound 33).

To a stirred solution of Compound 31 (0.055 g, 0.10 mmol) in dichloromethane (15 mL), ethyldicarbodiimide hydrochloride (0.048 g, 0.252 mmol) and 4-methylmorpholine (0.051 g, 0.504 mmol) were added and the solution was stirred at room temperature for 2 hours. It was then cooled to −78° C. and ammonia gas was bubbled through the solution for 45 minutes. The reaction mixture was allowed to stir at room temperature for 24 hours. The solution was concentrated, partitioned between dichloromethane (30 mL) and saturated solution of ammonium chloride (20 mL). The organic layer was dried over sodium sulfate, filtered and concentrated. Purification by column chromatography yielded 0.025 g (45%) of the product as a syrup. Hydrochloride salt (recrystallized from ether): yellow solid; m.p. 210–212° C. Analysis calculated for $C_{26}H_{31}Cl_2F_3N_6O_3$.2.10 $C_4H_{10}O$: C, 54.43; H, 5.80; N, 11.07. Found: C, 54.61; H, 5.36; N, 11.38.

34. 4-Aminocarbonyl-1-(5-(4-(2-aminocarbonylphenyl)piperazin-1-yl)pent-1-yl)-5-(3,4-difluorophenyl)-2,3-dihydro-2(1H)-imidazolone (Compound 34).

To a stirred solution Compound 32 (0.108 g, 0.18 mmol) in dichloromethane (15 mL), ethyldicarbodiimide hydrochloride (0.088 g, 0.46 mmol) and 4-methylmorpholine (0.093 g, 0.92 mmol) were added and the solution was stirred at room temperature for 2 hours. It was then cooled to −78° C. and ammonia gas was bubbled through the solution for 45 minutes. The reaction mixture was allowed to stir at room temperature for 24 hours. The solution was concentrated, partitioned between dichloromethane (30 mL) and saturated solution of ammonium chloride (20 mL). The organic layer was dried over sodium sulfate, filtered and concentrated. Purification by column chromatography yielded 0.06 g (56%) of the product as a syrup. Hydrochloride salt (recrystallized from ether): light yellow solid; m.p. 172–174° C.

35. 5-(3,4-Difluorobenzyl)-2,3-dihydro-4-methoxycarbonyl-1-(5-(4-phenylpiperidin-1-yl)pent-1-yl)-2(1H)-imidazolone (Compound 35).

Step A: 5-(3,4-Difluorobenzyl)-4-methoxycarbonyloxazole.

3,4-Difluorophenylacetic acid (3.61 g, 20.9 mmol) in oxalyl chloride (7.31 ml, 83.8 mmol) was refluxed for 4 hours. The solution was cooled to room temperature, concentrated under reduced pressure to give 3,4-difluorophenylacetyl chloride which was used without purification. To a well stirred solution of 3,4-difluorophenylacetyl chloride (2.21 g, 11.59 mmol) in THF (10 mL) was added 1,8-diazabicyclo[5.4.0]undec-7-ene (DBU) (3.47 mL, 23.18 mmol) at room temperature and the solution was stirred for five minutes. Then methylisocyanoacetate (1.55 mL, 11.59 mmol) was added over a three minute period to the reaction mixture. After stirring for 18 hours at room temperature, the reaction mixture was partitioned between ether (100 mL) and water (50 mL). The organic layer was washed with 1N HCl (10 mL), water (15 mL) and saturated solution of sodium bicarbonate (15 mL), and dried over sodium sulfate. The solution was then filtered and concentrated. The residue was chromatographed (hexanes:EtOAc, 3:2) to yield 100 mg (3.4%) of the product; $^1$H-NMR (CDCl$_3$) δ3.89 (s, 3H), 6.98 (s, 2H), 7.00–7.09 (m, 3H), 7.73 (s, 1H).

Step B: 2-Amino-4-(3,4-difluorophenyl)-3-oxobutyric acid methyl ester.

To 5-(3,4-difluorobenzyl)-4-methoxycarbonyloxazole (0.100 g, 0.393 mmol) in methanol (5 mL) was added 2 mL of 6N HCl, and the solution heated at 80° C. for 2 hours. The reaction mixture was concentrated to yield 0.100 g (88%) of a solid which was used as such for the subsequent step.

Step C: 1-(5-Bromopent-1-yl)-5-(3,4-difluorobenzyl)-2,3-dihydro-4-methoxycarbonyl-2(1H)-imidazolone.

To 2-amino-4-(3,4-difluorophenyl)-3-oxobutyric acid methyl ester (0.100 g, 0.344 mmol) in 2 mL water was added 1-bromo-5-isocyanatopentane (0.3 mL), and the reaction mixture refluxed for 3 hours. The reaction mixture was concentrated and partitioned between EtOAc (30 mL) and 1N HCl (10 mL). The organic layer was washed with saturated aqueous sodium bicarbonate solution (10 mL), dried over sodium sulfate, filtered and concentrated to give 0.080 g (55%) of the product as a syrup; $^1$H-NMR (CDCl$_3$) δ1.36–1.81 (m, 6 H), 3.34 (t, J=6.6 Hz, 2 H), 3.32–3.37 (m, 2 H), 3.86 (s, 3 H), 4.21 (s, 2 H), 6.91–7.16 (m, 3 H), 9.53 (s, 1 H).

Step D: 5-(3,4-Difluorobenzyl)-2,3-dihydro-4-methoxycarbonyl-1-(5-(4-phenylpiperidin-1-yl)pent-1-yl)-2(1H)-imidazolone.

To a stirred solution of 1-(5-bromopent-1-yl)-5-(3,4-difluorobenzyl)-2,3-dihydro-4-methoxycarbonyl-2(1H)-imidazolone (0.167 g, 0.4 mol) in dioxane (20 mL) was added 4-phenylpiperidine (0.128 g, 0.800 mmol), potassium carbonate (0.165 g, 1.20 mmol) and sodium iodide (0.358 g, 2.38 mmol), and the solution refluxed for 24 hours. The reaction mixture was cooled to room temperature, concentrated and partitioned between ethyl acetate (25 mL) and water (5 mL). The organic layer was dried over sodium sulfate, filtered and concentrated. The crude product was purified by column chromatography (ethyl acetate: methanol, 4.5:0.5) to yield 0.062 g (31%) of the required product as a colorless oil; $^1$H-NMR (CDCl$_3$) δ1.25–2.44 (m, 13H), 3.13 (d, J=11.4 Hz, 2H), 3.26 (d, J=10.5 Hz, 2H), 3.53 (t, J=7.7 Hz, 2H), 3.85 (s, 3H), 4.10–4.12 (m, 1H), 4.21 (s, 2H), 6.90–7.30 (m, 8H). Hydrochloride salt (recrystallized from ether): yellow solid; m.p. 130–132° C. Analysis calculated for $C_{28}H_{34}ClF_2N_3O_3 \cdot 0.80$ $CH_2Cl_2$: C, 57.46; H, 5.96; N, 6.98. Found: C, 57.18; H, 6.33; N, 6.76.

The following compounds were similarly prepared.

36. 5-(4-Fluorobenzyl)-2,3-dihydro-4-methoxycarbonyl-1-(3-(4-methoxycarbonyl-4-phenylpiperidin-1-yl)prop-1-yl)-2 (1H)-imidazolone (Compound 36).

Hydrochloride salt: yellow solid; m.p. 215–217° C.

37. 5-(3,4-Difluorobenzyl)-2,3-dihydro-4-methoxycarbonyl-1-(5-(4-methoxycarbonyl-4-phenylpiperidin-1-yl)pent-1-yl)-2(1H) -imidazolone (Compound 37).

Hydrochloride salt: pale yellow solid; m.p. 180–184° C.

38. 5-(3,4-Difluorobenzyl)-2,3-dihydro-4-methoxycarbonyl-1-(5-(4,4-diphenylpiperidin-1-yl)pent-1-yl)-2(1H)-imidazolone (Compound 38).

Hydrochloride salt (recrystallized from ether): white solid; m.p. 120–122° C. Scheme 2 (Diagram below)

39. 5-(3,4-Difluorophenyl)-2,3-dihydro-4-methoxycarbonyl-1-(3-(4-(2-methoxyphenyl)piperazin-1-yl)prop-1-yl)aminocarbonyl-2(1H)-imidazolone (Compound 39).

Step A: N-(3-Bromo-1-propyl)isocyanatoformamide.

To 3-bromo-1-propylamine hydrobromide (1.0 g, 4.56 mmol) in THF (20 mL) was added triethylamine (2.31 g, 22.8 mmol). The mixture was cooled to −78° C., triturated with N-(chlorocarbonyl)isocyanate (723 mg, 6.85 mmol) and stirred for 10 min. It was then concentrated, and the residue was partitioned between EtOAc and water. The organic layer was dried over Na$_2$SO$_4$, filtered and concentrated to give, in quantitative yield, the crude product which was used without purification.

Step B: 5-(3,4-Difluorophenyl)-2,3-dihydro-4-methoxycarbonyl-1-(3-bromoprop-1-yl)aminocarbonyl-2 (1H)-imidazolone.

A mixture of 2-amino-3-(3,4-difluorophenyl)-3-oxopropionic acid methyl ester hydrochloride (743 mg, 2.80 mmol) and N-(3-bromo-1-propyl)isocyanatoformamide (1.345 g, 6.5 mmol) in dioxane (15 mL) was heated at reflux for 24 hours and then concentrated. The residue was partitioned between EtOAc and 1N HCl. The organic layer was washed with aqueous NaHCO$_3$, dried over Na$_2$SO$_4$, filtered and concentrated to give, in quantitative yield, the crude product which was used without purification.

Step C: 5-(3,4-Difluorophenyl)-2,3-dihydro-4-methoxycarbonyl-1-(3-(4-(2-methoxyphenyl)piperazin-1-yl)prop-1-yl)aminocarbonyl-2(1H)-imidazolone.

A mixture of 5-(3,4-difluorophenyl)-2,3-dihydro-4-methoxycarbonyl-1-(3-bromoprop-1-yl)aminocarbonyl-2 (1H)-imidazolone (386 mg, 0.92 mmol), 4-(2-methoxyphenyl)piperazine (353 mg, 1.84 mmol), potassium carbonate (382 mg, 2.76 mmol) and sodium iodide (138 mg, 0.92 mmol) in dioxane (15 mL) was heated at reflux for 24 hours and then concentrated. The residue was partitioned between EtOAc and water. The organic layer was dried over Na$_2$SO$_4$, filtered and concentrated to give the crude product which was flash chromatographed over silica gel eluting with EtOAc/MeOH (9:1) to give the desired product (2% yield). Hydrochloride salt: yellow solid; m.p. 122–124° C.

40. 5-(3,4-Difluorophenyl)-2,3-dihydro-4-methoxycarbonyl-1-(3-(4-methoxycarbonyl-4-phenylpiperidin-1-yl)prop-1-yl)aminocarbonyl-2(1H)-imidazolone (Compound 40).

Step A: 1-Trichloroacetyl-5-(3,4-difluorophenyl)-2,3-dihydro-4-methoxycarbonyl-2(1H)-imidazolone.

A mixture of 2-amino-3-(3,4-difluorophenyl)-3-oxopropionic acid methyl ester hydrochloride (671 mg, 2.53 mmol) and N-trichloroacetylisocyanate (1.93 g, 10.2 mmol) in dioxane (10 mL) was heated at reflux for 24 hours and then concentrated. The residue was partitioned between EtOAc and 1N HCl. The organic layer was washed with aqueous NaHCO$_3$, dried over Na$_2$SO$_4$, filtered and concentrated to give, in quantitative yield, the crude product which was used without purification.

Step B: 5-(3,4-Difluorophenyl)-2,3-dihydro-4-methoxycarbonyl-1-(3-(4-methoxycarbonyl-4-phenylpiperidin-1-yl)prop-1-yl) aminocarbonyl-2(1H)-imidazolone.

A mixture of 1-trichloroacetyl-5-(3,4-difluorophenyl)-2, 3-dihydro-4-methoxycarbonyl-2(1H)-imidazolone (583 mg, 1.46 mmol), 1-(3-aminopropyl)-4-methoxycarbonyl-4-phenylpiperidine (808 mg, 2.92 mmol) and potassium carbonate (809 mg, 5.85 mmol) in dioxane (15 mL) was heated at reflux for 24 hours and then concentrated. The residue was partitioned between EtOAc and water. The organic layer was dried over Na$_2$SO$_4$, filtered and concentrated to give the crude product which was flash chromatographed over silica gel to give the product (15 mg, 2% yield). Hydrochloride salt: light brown solid; m.p. 134–136° C.

II. General Syntheses of Imidazolones

The examples described above are merely illustrative of the methods used to synthesize imidazolones. Further derivatives may be obtained utilizing the methods shown in Schemes 3–12. The substituents in Schemes 3–12 are described in the Detailed Description.

It may be necessary to incorporate protection and deprotection strategies for substituents such as amino, amido, carboxylic acid, and hydroxyl groups in the synthetic methods described above to form imidazolones. Methods for protection/deprotection of such groups are well-known in the art, and may be found, for example in Greene, T. W. and Wuts, P. G. M. (1991) *Protective Groups in Organic Synthesis,* 2nd Edition John Wiley & Sons, New York.

III. Oral Composition

As a specific embodiment of an oral composition of a compound of this invention, 100 mg of one of the compounds described herein is formulated with sufficient finely divided lactose to provide a total amount of 580 to 590 mg to fill a size O hard gel capsule.

IV. Pharmacological Profiles of the Compounds in Cloned Human Adrenergic Receptors.

Binding affinities were measured for selected compounds of the invention at six cloned human $\alpha_1$ and $\alpha_2$ receptor subtypes, as well as at the L-type calcium channel. The protocols for these experiments are given below.

1. Protocol for the Determination of the Potency of $\alpha_1$ Antagonists

The activity of compounds at the different human receptors was determined in vitro using cultured cell lines that selectively express the receptor of interest. These cell lines were prepared by transfecting the cloned cDNA or cloned genomic DNA or constructs containing both genomic DNA and cDNA encoding the human α-adrenergic receptors as follows:

$\alpha_{1d}$ Human Adrenergic Receptor: The entire coding region of $\alpha_{1d}$ (1719 bp), including 150 base pairs of 5' untranslated sequence (5' UT) and 300 bp of 3' untranslated sequence (3' UT), was cloned into the BamHI and ClaI sites of the polylinker-modified eukaryotic expression vector pCEXV-3, called EXJ.HR. The construct involved the ligation of partial overlapping human lymphocyte genomic and hippocampal cDNA clones: 5' sequence were contained on a 1.2 kb SmaI-XhoI genomic fragment (the vector-derived BamHI site was used for subcloning instead of the internal insert-derived SmaI site) and 3' sequences were contained on an 1.3 kb XhoI-ClaI cDNA fragment (the ClaI site was from the vector polylinker). Stable cell lines were obtained by cotransfection with the plasmid α1A/EXJ (expression vector containing the $\alpha_{1a}$ receptor gene (old nomenclature)) and the plasmid pGCcos3neo (plasmid containing the aminoglycoside transferase gene) into LM(tk-) cells using calcium phosphate technique. The cells were grown, in a controlled environment (37° C., 5% $CO_2$), as monolayers in Dulbecco's modified Eagle's Medium (GIBCO, Grand Island, N.Y.) containing 25 mM glucose and supplemented with 10% bovine calf serum, 100 units/ml penicillin g, and 100 μg/ml streptomycin sulfate. Stable clones were then selected for resistance to the antibiotic G-418 (1 mg/ml), and membranes were harvested and assayed for their ability to bind [$^3$H]prazosin as described below (see "Radioligand Binding assays").

The cell line expressing the human $\alpha_{1d}$ receptor used herein was designated L-$\alpha_{1A}$ (old nomenclature) and was deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure. The cell line expressing the human $\alpha_{1d}$ receptor, was accorded ATCC Accession No. CRL 11138, and was deposited on Sep. 25, 1992.

$\alpha_{1b}$ Human Adrenergic Receptor: The entire coding region of $\alpha_{1b}$ (1563 bp), including 200 base pairs and 5' untranslated sequence (5' UT) and 600 bp of 3' untranslated sequence (3' UT), was cloned into the EcoRI site of pCEXV-3 eukaryotic expression vector. The construct involved ligating the full-length containing EcoRI brainstem cDNA fragment from λ ZapII into the expression vector. Stable cell lines were selected as described above. The cell line used herein was designated L-$\alpha_{1B}$ and was deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure. The cell line L-$\alpha_{1B}$ was accorded ATCC Accession No. CR 11139, on Sep. 29, 1992.

$\alpha_{1a}$ Human Adrenergic Receptor: The entire coding region of $\alpha_{1a}$ (1401 bp), including 400 base pairs of 5' untranslated sequence (5' UT) and 200 bp of 3' untranslated sequence (3' UT), was cloned into the KpnI site of the polylinker-modified pCEXV-3-derived eukaryotic expression vector, EXJ.RH. The construct involved ligating three partial overlapping fragments: a 5' 0.6 kb HincII genomic clone, a central 1.8 EcoRI hippocampal cDNA clone, and a 3' 0.6Kb PstI genomic clone. The hippocampal cDNA fragment overlaps with the 5' and 3' genomic clones so that the HincII and PstI sites at the 5' and 3' ends of the cDNA clone, respectively, were utilized for ligation. This full-length clone was cloned into the KpnI site of the expression vector, using the 5' and 3' KpnI sites of the fragment, derived from vector (i.e., pBluescript) and 3'-untranslated sequences, respectively. Stable cell lines were selected as described above. The stable cell line expressing the human $\alpha_{1a}$ receptor used herein was designated L-$\alpha_{1C}$ (old nomenclature) and was deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure. The cell line expressing the human $\alpha_{1a}$ receptor was accorded Accession No. CR 11140, on Sep. 25, 1992.

Radioligand Binding Assays for $\alpha_1$ receptors:

Transfected cells from culture flasks were scraped into 5 ml of 5 mM Tris-HCl, 5 mM EDTA, pH 7.5, and lysed by sonication. The cell lysates were centrifuged at 1000 rpm for 5 min at 4° C., and the supernatant was centrifuged at 30,000× g for 20 min at 4° C. The pellet was suspended in 50 mM Tris-HCl, 1 mM $MgCl_2$, and 0.1% ascorbic acid at pH 7.5. Binding of the $\alpha_1$ antagonist [$^3$H]prazosin (0.5 nM, specific activity 76.2 Ci/mmol) to membrane preparations of LM(tk-) cells was done in a final volume of 0.25 ml and incubated at 37° C. for 20 min. Nonspecific binding was determined in the presence of 10 μg phentolamine. The reaction was stopped by filtration through GF/B filters using a cell harvester. Inhibition experiments, routinely consisting of 7 concentrations of the tested compounds, were analyzed using a non-linear regression curve-fitting computer program to obtain Ki values.

$\alpha_2$ Human Adrenergic Receptors: To determine the potency of $\alpha_1$ antagonists at the $\alpha_2$ receptors, LM(tk-) cell lines stably transfected with the genes encoding the $\alpha_{2a}$, $\alpha_{2b}$, and $\alpha_{2c}$ receptors were used. The cell line expressing the $\alpha_{2a}$ receptor is designated L-$\alpha_{2A}$, and was deposited on Nov. 6, 1992 under ATCC Accession No. CRL 11180. The cell line expressing the $\alpha_{2b}$ receptor is designated L-NGC-$\alpha_{2B}$, and was deposited on Oct. 25, 1989 under ATCC Accession No. CRL10275. The cell line expressing the $\alpha_{2c}$ receptor is designated L-$\alpha_{2C}$, and was deposited on Nov. 6, 1992 under ATCC Accession No. CRL-11181. All the cell lines were deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure. Cell lysates were prepared as described above (see Radioligand Binding Assays), and suspended in 25 mM glycylglycine buffer (pH 7.6 at room temperature). Equilibrium competition binding assay were performed using [3H]rauwolscine (0.5 nM), and nonspecific binding was determined by incubation with 10 μM phentolamine. The bound radioligand was separated by filtration through GF/B filters using a cell harvester.

Determination of the Activity of $\alpha_1$ Antagonists at Calcium Channels:

The potency of $\alpha_1$ antagonists at calcium channels may be determined in competition binding assays of [3H] nitrendipine to membrane fragments of rat cardiac muscle, essentially as described by Glossman and Ferry (Methods in Enzymology 109:513–550, 1985). Briefly, the tissue is minced and homogenized in 50 mM Tris-HCl (pH 7.4) containing 0.1 mM phenylmethylsulfonyl fluoride. The homogenates are centrifuged at 1000 g for 15 minutes, and the resulting supernatant centrifuged at 45,000 g for 15 minutes. The 45,000 g pellet is suspended in buffer and centrifuged a second time. Aliquots of membrane protein are then incubated for 30 minutes at 37° C. in the presence of [3H]nitrendipine (1 nM), and nonspecific binding determined in the presence of 10 µg nifedipine. The bound radioligand is separated by filtration through GF/B filters using a cell harvester.

The compounds described above were assayed using cloned human alpha adrenergic receptors. The preferred compounds were found to be selective $\alpha_{1a}$ antagonists. The binding affinities of several compounds are illustrated in the following table.

Binding affinities of selected compounds of the present invention at cloned human $\alpha_{1d}$, $\alpha_{1b}$ and $\alpha_{1a}$ receptors. (h=human)

| Compound | h$\alpha_{1d}$ $K_i$ (nM) | h$\alpha_{1b}$ $K_i$ (nM) | h$\alpha_{1a}$ $K_i$ (nM) |
| --- | --- | --- | --- |
| 1 | 328.6 | 309.0 | 1.8 |
| 2 | 367.3 | 346.7 | 4.1 |
| 3 | 2660.7 | 1584.9 | 21.1 |
| 4 | 278.6 | 159.4 | 1.5 |
| 5 | 15.7 | 11.7 | 0.1 |
| 6 | 141.3 | 109.6 | 1.4 |
| 7 | 197.2 | 110.9 | 1.2 |
| 37 | 512.9 | 558.0 | 4.5 |

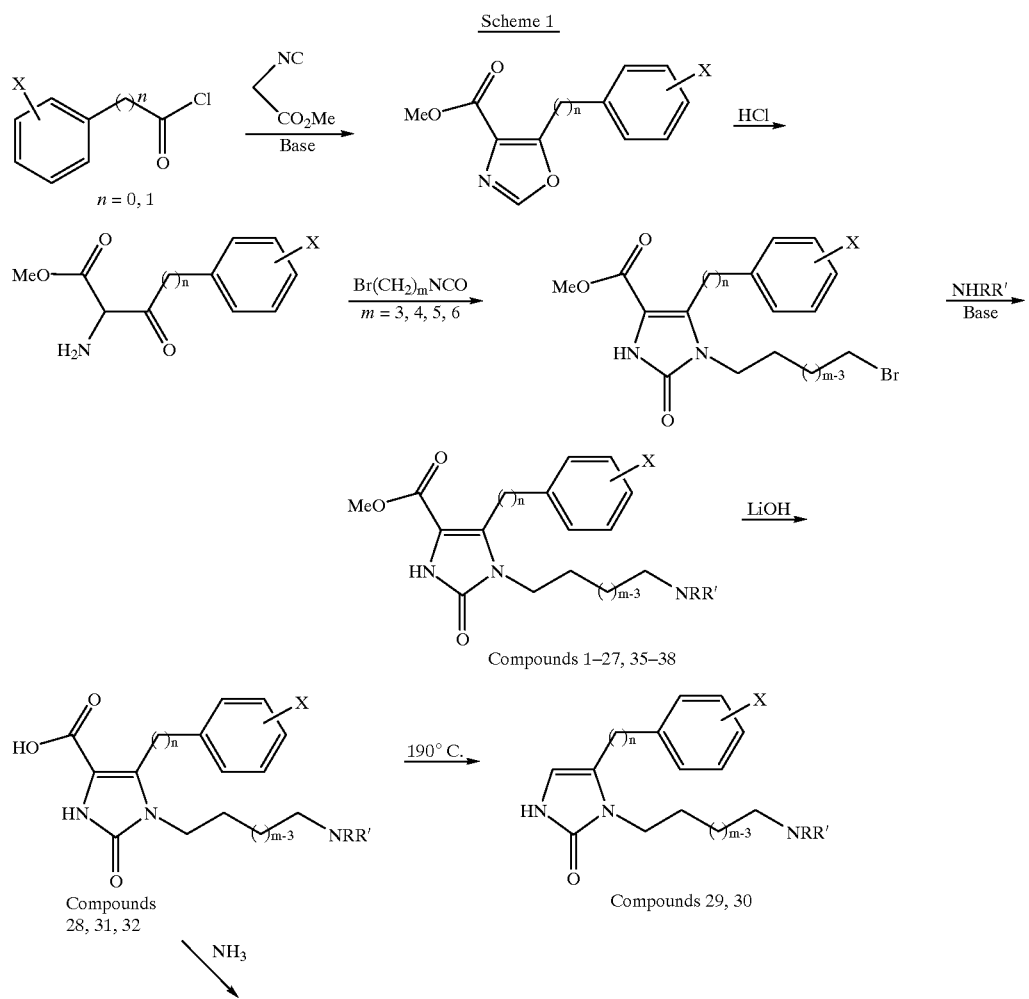

Scheme 1

-continued
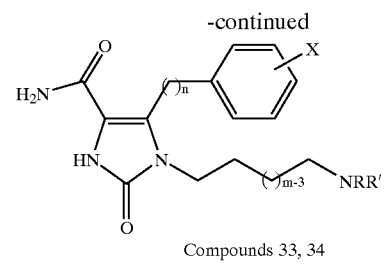
Compounds 33, 34
Scheme 2
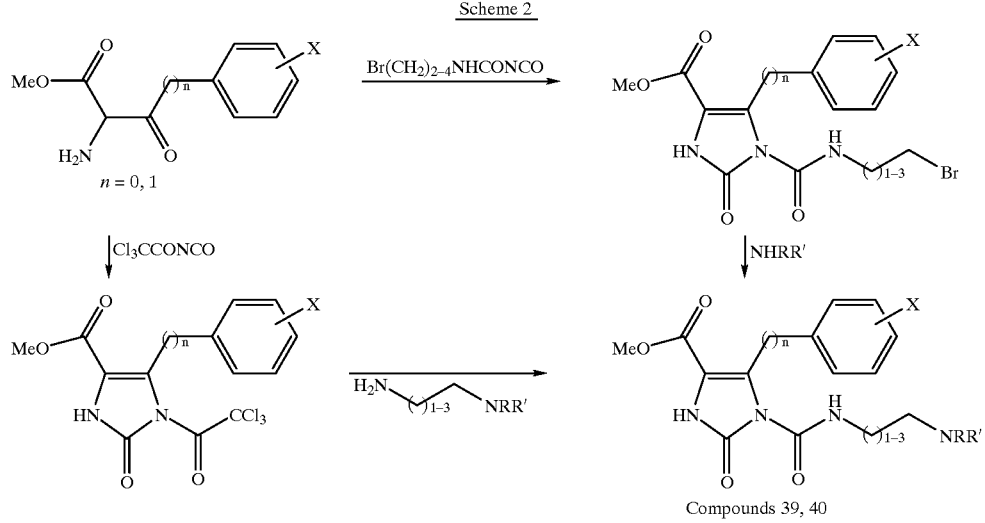
Compounds 39, 40
Scheme 3: General Synthesis of Compounds.
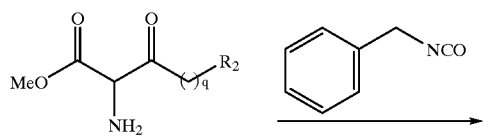
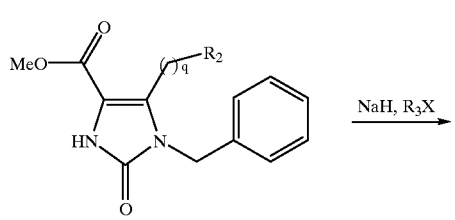
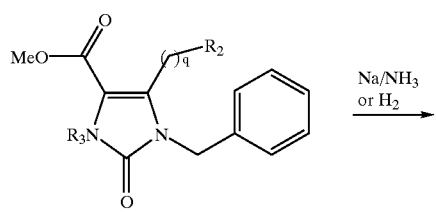
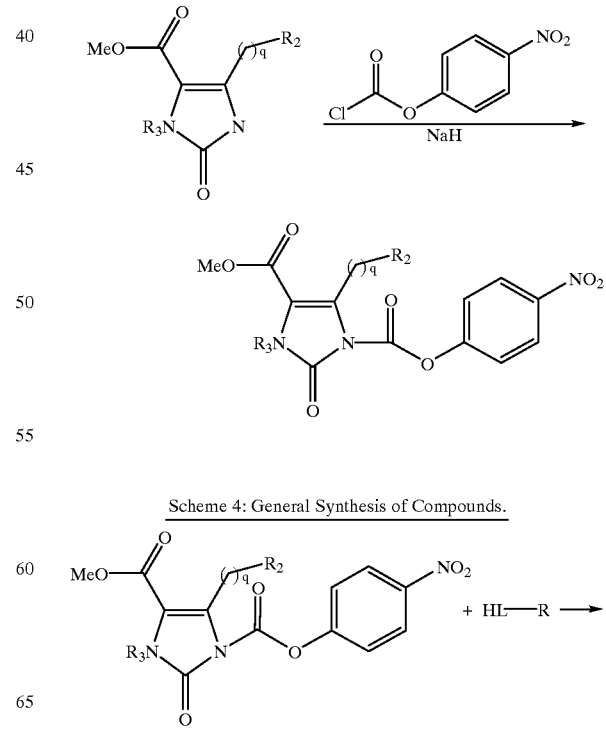
Scheme 4: General Synthesis of Compounds.

-continued
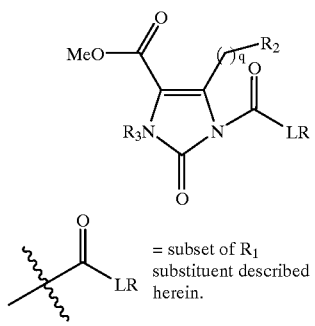
Scheme 5: General Synthesis of Compounds.
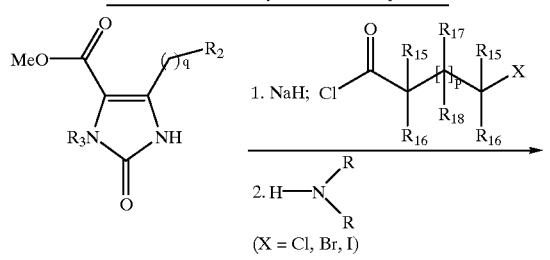
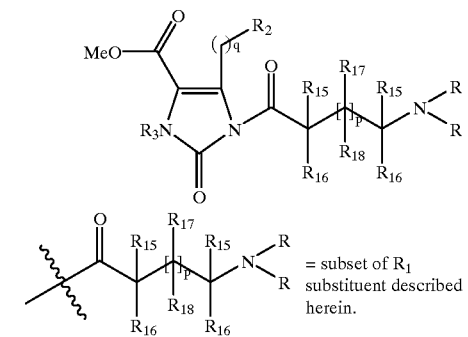
Scheme 6: General Synthesis of Compounds.
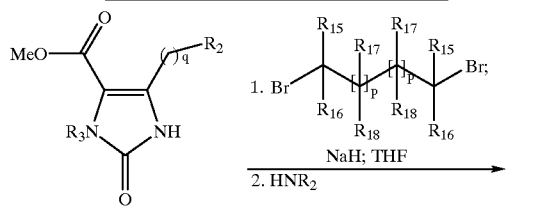
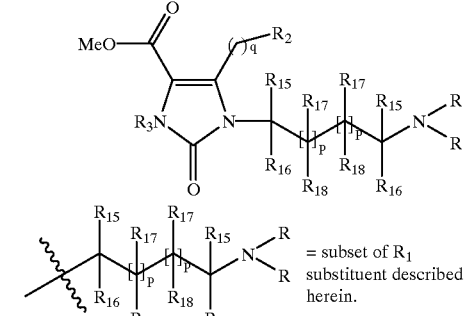
Scheme 7: General Synthesis of Compounds.
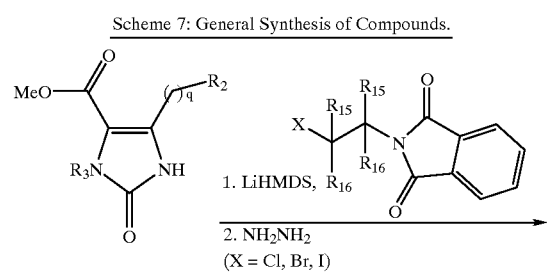
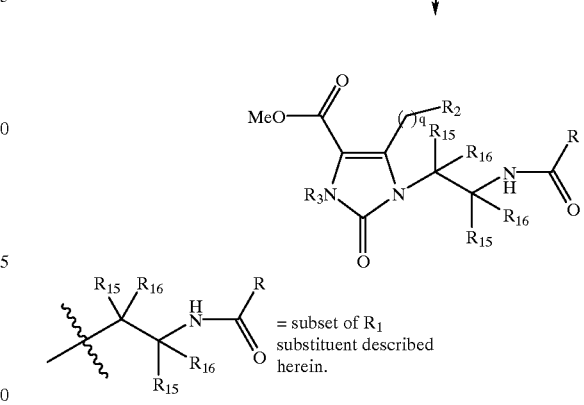
Scheme 8: General Synthesis of Compounds.
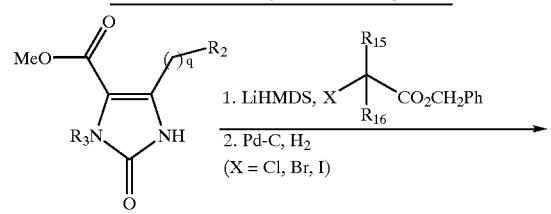
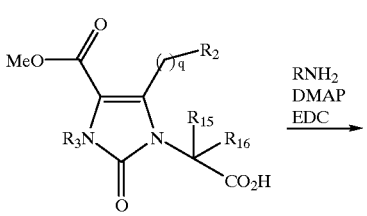

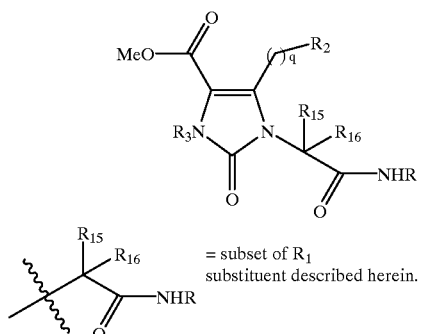
= subset of $R_1$ substituent described herein.
Scheme 9: General Synthesis of Compounds.
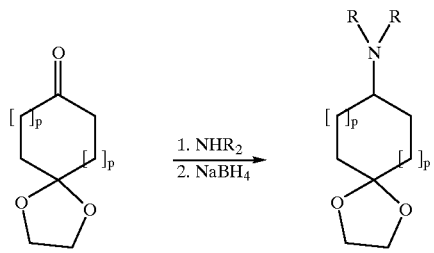
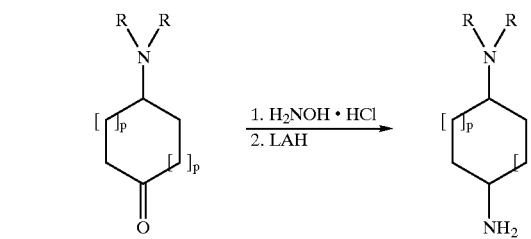
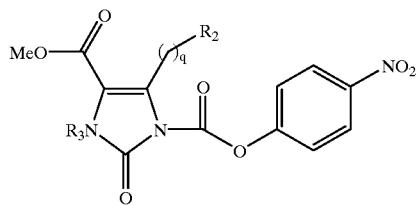
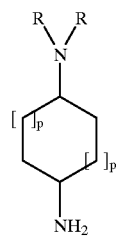
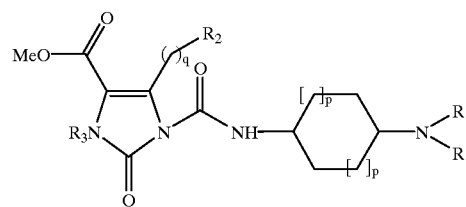
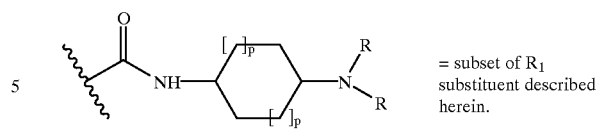
= subset of $R_1$ substituent described herein.
Scheme 10: General Synthesis of Compounds.
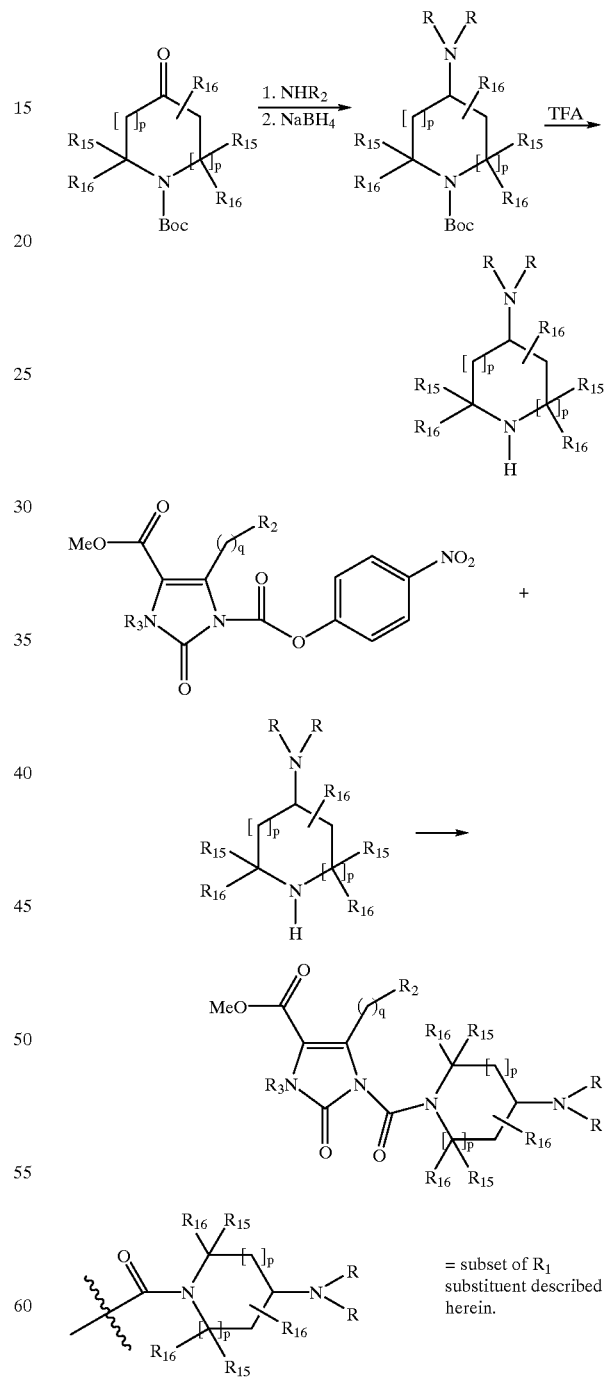
= subset of $R_1$ substituent described herein.

Scheme 11: General Synthesis of Compounds.

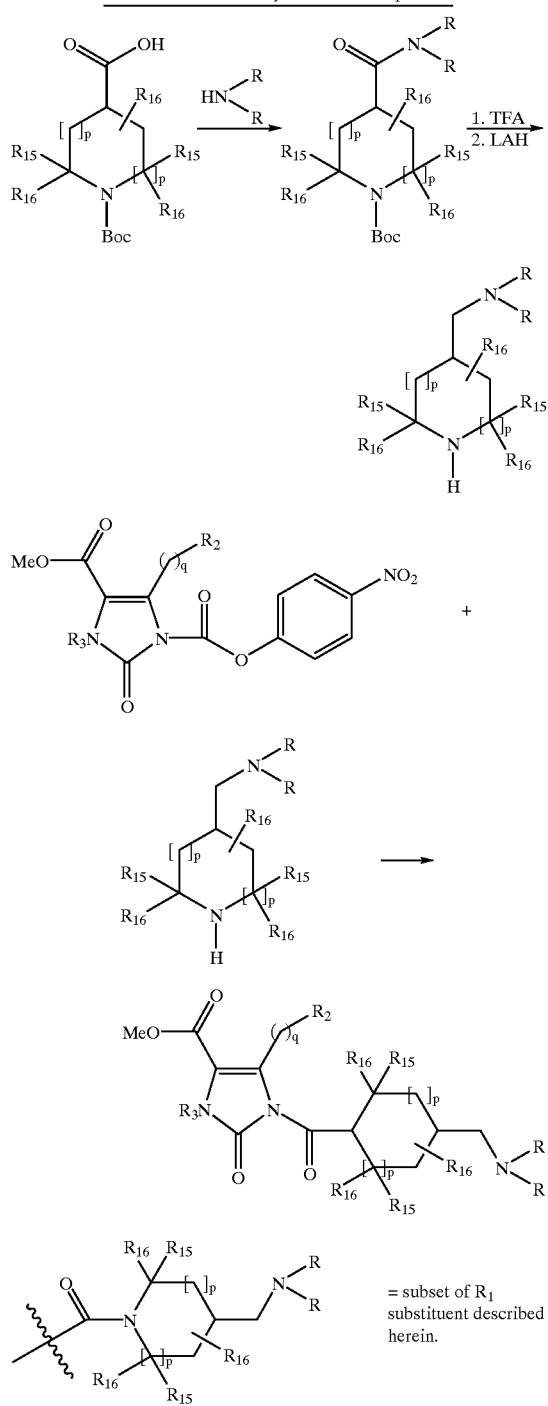

Scheme 12: General Synthesis of Compounds.

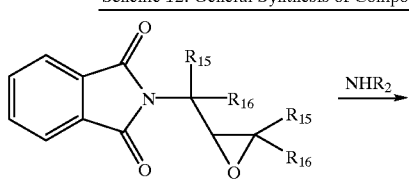

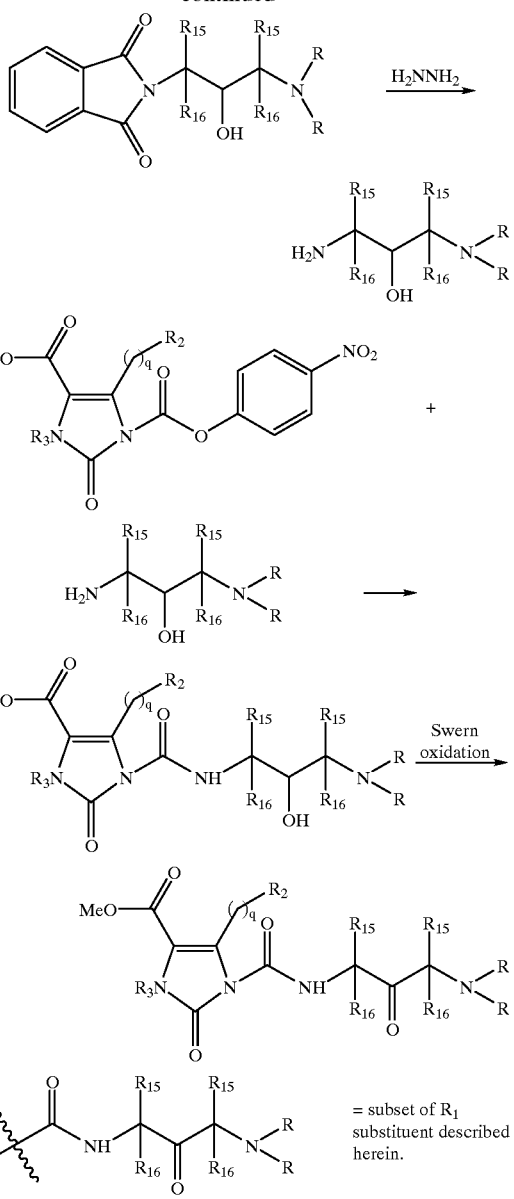

What is claimed is:

1. A compound having the structure

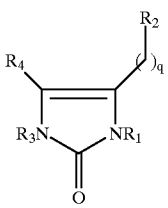

where $R_2$ is aryl or heteroaryl; wherein the aryl or heteroaryl is unsubstituted or substituted with one or more of F; Cl; Br; I; —CN; —NO$_2$; —N(R$_8$)$_2$; —SO$_2$R$_8$; —SO$_2$N (R$_8$)$_2$; —(CH$_2$)$_n$C(Y)R$_8$; —(CH$_2$)$_n$YR$_8$; —(CH$_2$)$_n$C(Y)N(R$_8$)$_2$; —(CH$_2$)$_n$CO$_2$R$_8$; methylenedioxy; straight chained or branched C$_1$–C$_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl;

where $R_3$ is independently H; straight chained or branched $C_1$–$C_7$ alkyl, alkoxyalkyl, monofluoroalkyl, or polyfluoroalkyl;

where $R_4$ is H, —$(CH_2)_tYR_8$, —$(CH_2)_tC(Y)N(R_8)_2$, —$(CH_2)_tC(Y)R_8$, —$(CH_2)_tCO_2R_8$, —$(CH_2)_tN(R_8)_2$, —$(CH_2)_tCN$, —$C(Y)R_8$, —$C(Y)N(R_8)_2$, —$CO_2R_8$, straight chained or branched $C_1$–$C_7$ alkyl, straight chained or branched $C_2$–$C_7$ alkenyl or alkynyl, $C_3$–$C_7$ cycloalkyl, $C_5$–$C_7$ cycloalkenyl, or phenyl or benzyl; wherein the phenyl or benzyl is unsubstituted or substituted with one or more of F; Cl; Br; I; —CN; —$NO_2$; —$N(R_8)_2$; —$SO_2R_8$; —$SO_2N(R_8)_2$; —$(CH_2)_nC(Y)R_8$; —$(CH_2)_nYR_8$; —$(CH_2)_nC(Y)N(R_8)_2$; —$(CH_2)_nCO_2R_8$; methylenedioxy; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl;

where each $R_8$ is independently H, straight chained or branched $C_1$–$C_7$ alkyl, straight chained or branched $C_2$–$C_7$ alkenyl or alkynyl, $C_3$–$C_7$ cycloalkyl, $C_5$–$C_7$ cycloalkenyl, or polyfluoroalkyl;

where q is an integer from 0 to 4 inclusive;

where each n independently is an integer from 0 to 7 inclusive;

where each t independently is an integer from 1 to 4 inclusive;

where each Y is independently O or S;

where $R_1$ is

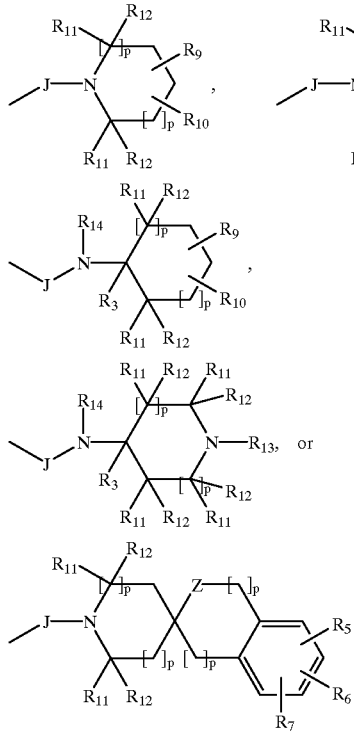

wherein $R_5$, $R_6$, and $R_7$ independently are H; F; Cl; Br; I; —CN; —$NO_2$; —$N(R_8)_2$; —$SO_2R_8$; —$(CH_2)_nC(Y)R_8$; —$(CH_2)_nYR_8$; —$(CH_2)_nC(Y)N(R_8)_2$; —$(CH_2)_nCO_2R_8$; —$SO_2N(R_8)_2$; methylenedioxy; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl;

wherein each $R_9$ is H; straight chained or branched $C_1$–$C_7$ alkyl, hydroxyalkyl, aminoalkyl, alkoxyalkyl, monofluoroalkyl, or polyfluoroalkyl; straight chained or branched $C_2$–$C_7$ alkenyl or alkynyl; $C_3$–$C_7$ cycloalkyl, monofluorocycloalkyl, or polyfluorocycloalkyl; $C_5$–$C_7$ cycloalkenyl; or aryl or heteroaryl; wherein the aryl or heteroaryl is unsubstituted or substituted with one or more of F; Cl; Br; I; —$(CH_2)_nYR_8$; —$(CH_2)_nC(Y)R_8$; —$(CH_2)_nC(Y)N(R_8)_2$; —$(CH_2)_nCO_2R_8$; —CN; —$NO_2$; —$N(R_8)_2$; —$SO_2R_8$; —$SO_2N(R_8)_2$; methylenedioxy; straight chained or branched $C_1$–$C_7$ alkyl, monofluoroalkyl, or polyfluoroalkyl; straight chained or branched $C_2$–$C_7$ alkenyl or alkynyl; $C_3$–$C_7$ cycloalkyl, monofluorocycloalkyl, or polyfluorocycloalkyl; or $C_5$–$C_7$ cycloalkenyl;

wherein each $R_{10}$ is H; F; —OH; —$(CH_2)_nC(Y)R_8$; —$(CH_2)_nYR_8$; —$(CH_2)_nC(Y)N(R_8)_2$; —$(CH_2)_nCO_2R_8$; —CN; —$NO_2$; —$N(R_8)_2$; aryl or heteroaryl; straight chained or branched $C_1$–$C_7$ alkyl, hydroxyalkyl, aminoalkyl, carboxamidoalkyl, alkoxyalkyl, monofluoroalkyl, or polyfluoroalkyl; straight chained or branched $C_2$–$C_7$ alkenyl or alkynyl; $C_3$–$C_7$ cycloalkyl, monofluorocycloalkyl, or polyfluorocycloalkyl; or $C_5$–$C_7$ cycloalkenyl; wherein the alkyl, hydroxyalkyl, alkoxyalkyl, aminoalkyl, carboxamidoalkyl, alkenyl, alkynyl, cycloalkyl or cycloalkenyl is unsubstituted or substituted with one or more aryl or heteroaryl; wherein the aryl or heteroaryl is unsubstituted or substituted with one or more of F; Cl; Br; I; —$(CH_2)_nYR_8$; —$(CH_2)_nC(Y)R_8$; —$(CH_2)_nC(Y)N(R_8)_2$; —$(CH_2)_nCO_2R_8$; —CN; —$NO_2$; —$N(R_8)_2$; —$SO_2R_8$; —$SO_2N(R_8)_2$; methylenedioxy; straight chained or branched $C_1$–$C_7$ alkyl, monofluoroalkyl, or polyfluoroalkyl; straight chained or branched $C_2$–$C_7$ alkenyl or alkynyl; $C_3$–$C_7$ cycloalkyl, monofluorocycloalkyl, or polyfluorocycloalkyl; or $C_5$–$C_7$ cycloalkenyl;

wherein each $R_{11}$ is independently H, —$(CH)_tYR_8$, —$(CH_2)_tC(Y)N(R_8)_2$, —$(CH_2)_tC(Y)R_8$, —$(CH_2)_tCO_2R_8$, —$(CH_2)_tN(R_8)_2$, —$(CH_2)_tCN$, —$C(Y)R_8$, —$C(Y)N(R_8)_2$, —$CO_2R_8$, straight chained or branched $C_1$–$C_7$ alkyl, straight chained or branched $C_2$–$C_7$ alkenyl or alkynyl, $C_3$–$C_7$ cycloalkyl, or $C_5$–$C_7$ cycloalkenyl;

wherein each $R_{12}$ is independently H, —$(CH_2)_tYR_8$, —$(CH_2)_tC(Y)N(R_8)_2$, —$(CH_2)_tC(Y)R_8$, —$(CH_2)_tCO_2R_8$, —$(CH_2)_tN(R_8)_2$, —$(CH_2)_tCN$, straight chained or branched $C_1$–$C_7$ alkyl, straight chained or branched $C_2$–$C_7$ alkenyl or alkynyl, $C_3$–$C_7$ cycloalkyl, or $C_5$–$C_7$ cycloalkenyl;

wherein $R_{13}$ is H, $C_1$–$C_7$ alkyl, —$C(O)R_2$, aryl or heteroaryl, $C_1$–$C_7$ alkyl substituted with one or two aryl, or $C_1$–$C_7$ alkyl substituted with one or two heteroaryl; wherein the aryl or heteroaryl is unsubstituted or substituted with one or more of F; Cl; Br; I; —CN; —$NO_2$; —$N(R_8)_2$; —$SO_2R_8$; —$SO_2N(R_8)_2$; —$(CH_2)_nC(Y)R_8$; —$(CH_2)_nYR_8$; —$(CH_2)_nC(Y)N(R_8)_2$; —$(CH_2)_nCO_2R_8$; methylenedioxy; straight chained or branched $C_1$–$C_7$ alkyl, monofluoroalkyl, polyfluoroalkyl, or carboxamidoalkyl; straight chained or branched $C_2$–$C_7$ aminoalkyl, alkenyl, or alkynyl; $C_3$–$C_7$ cycloalkyl; or $C_5$–$C_7$ cycloalkenyl;

wherein $R_{14}$ is H, straight chained or branched $C_1$–$C_7$ alkyl;

wherein Z is O, S, $NR_{14}$, CO, $CH_2$,

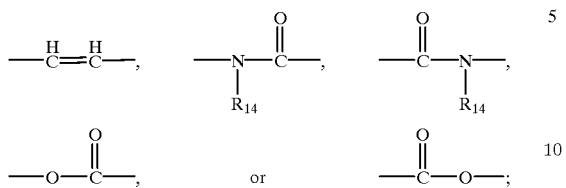

wherein each m is independently 1 or 2;

wherein each p is independently an integer from 0 to 2 inclusive;

wherein J is

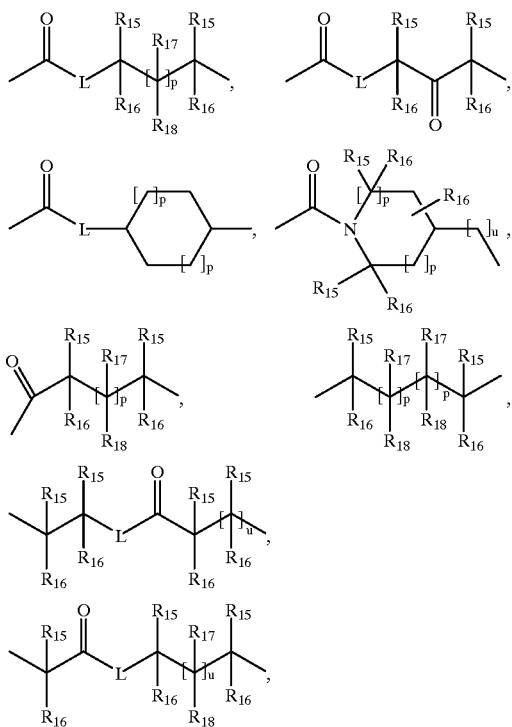

or $C_2$–$C_7$ alkenyl;

wherein each $R_{15}$ is independently H, —$(CH_2)_tYR_8$, —$(CH_2)_tC(Y)N(R_8)_2$, —$(CH_2)_tC(Y)R_8$, —$(CH_2)_tCO_2R_8$, —$(CH_2)_tN(R_8)_2$, —$(CH_2)_tCN$, —$C(Y)R_8$, —$C(Y)N(R_8)_2$, —$CO_2R_8$, straight chained or branched $C_1$–$C_7$ alkyl, straight chained or branched $C_2$–$C_7$ alkenyl or alkynyl, $C_3$–$C_7$ cycloalkyl, or $C_5$–$C_7$ cycloalkenyl;

wherein each $R_{16}$ is independently H, —$(CH_2)_tYR_8$, —$(CH_2)_tC(Y)N(R_8)_2$, —$(CH_2)_tC(Y)R_8$, —$(CH_2)_tCO_2R_8$, —$(CH_2)_tN(R_8)_2$, —$(CH_2)_tCN$, straight chained or branched $C_1$–$C_7$ alkyl, straight chained or branched $C_2$–$C_7$ alkenyl or alkynyl, $C_3$–$C_7$ cycloalkyl, or $C_5$–$C_7$ cycloalkenyl;

wherein each $R_{17}$ is independently H; F; —$(CH_2)_tYR_8$; —$(CH_2)_tC(Y)N(R_8)_2$; —$(CH_2)_tC(Y)R_8$; —$(CH_2)_tCO_2R_8$; —$(CH_2)_tN(R_8)_2$; —$(CH_2)_tCN$; —$C(Y)R_8$; —$C(Y)N(R_8)_2$; —$CO_2R_8$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl;

wherein each $R_{18}$ is independently H; F; —$(CH_2)_tYR_8$; —$(CH_2)_tC(Y)N(R_8)_2$; —$(CH_2)_tC(Y)R_8$; —$(CH_2)_tCO_2R_8$; —$(CH_2)_tN(R_8)_2$; —$(CH_2)_tCN$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl;

wherein L is S, O, or $N(R_8)$;

wherein u is an integer from 0 to 1 inclusive;

or a pharmaceutically acceptable salt thereof.

2. The compound of claim 1, wherein the compound comprises the (+) enantiomer.

3. The compound of claim 1, wherein the compound comprises the (−) enantiomer.

4. The compound of claim 1, wherein the compound has the structure:

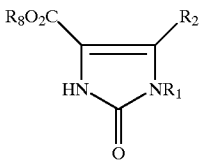

where $R_2$ is phenyl substituted with one or more of F; Cl; Br; I; —CN; —$NO_2$; —$N(R_8)_2$; —$SO_2R_8$; —$SO_2N(R_8)_2$; —$(CH_2)_nC(Y)R_8$; —$(CH_2)_nYR_8$; —$(CH_2)_nC(Y)N(R_8)_2$; —$(CH_2)_nCO_2R_8$; methylenedioxy; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl; and where $R_1$ is

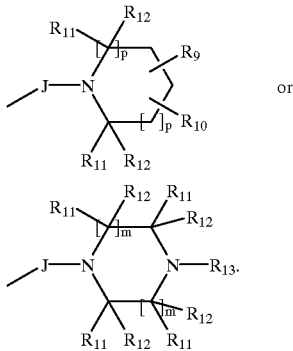

5. The compound of claim 4, where $R_1$ is

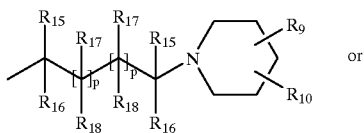

-continued

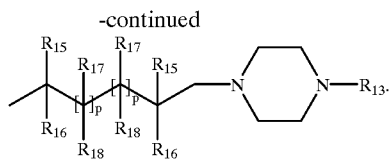

6. The compound of claim 5, wherein $R_9$ is phenyl or phenyl substituted with F; Cl; Br; I; —$(CH_2)_nYR_8$; —$(CH_2)_nC(Y)R_8$; —$(CH_2)_nC(Y)N(R_8)_2$; —$(CH_2)_nCO_2R_8$; —CN; —$NO_2$; —$N(R_8)_2$; —$SO_2R_8$; —$SO_2N(R_8)_2$; methylenedioxy; straight chained or branched $C_1$–$C_7$ alkyl, monofluoroalkyl, or polyfluoroalkyl; straight chained or branched $C_2$–$C_7$ alkenyl or alkynyl; $C_3$–$C_7$ cycloalkyl, monofluorocycloalkyl, or polyfluorocycloalkyl; or $C_5$–$C_7$ cycloalkenyl.

7. The compound of claim 1, wherein the compound is selected from the group consisting of:

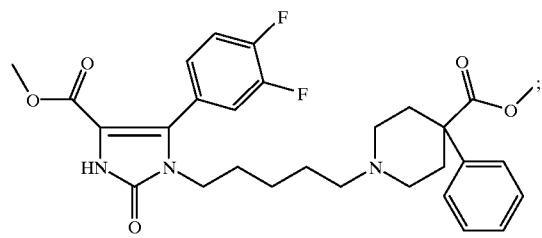

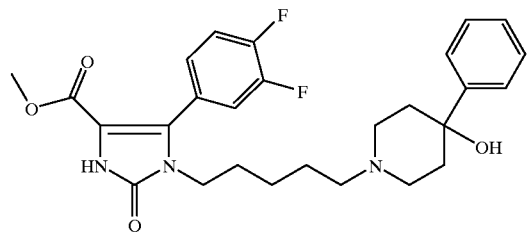

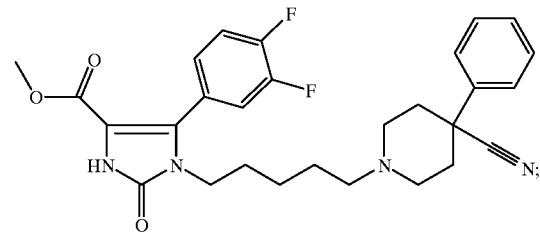

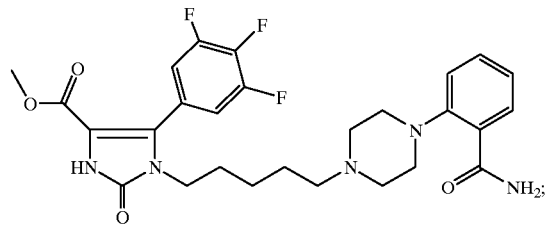

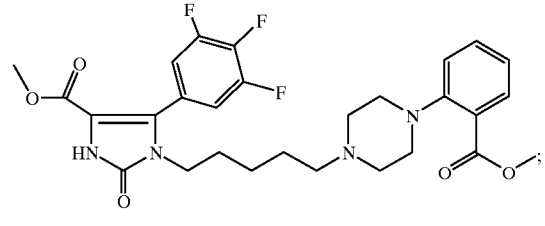

-continued

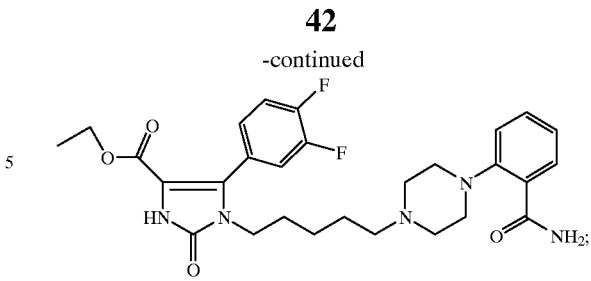

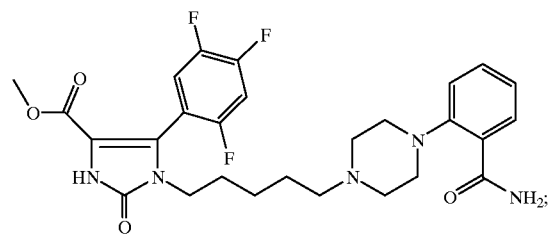

and

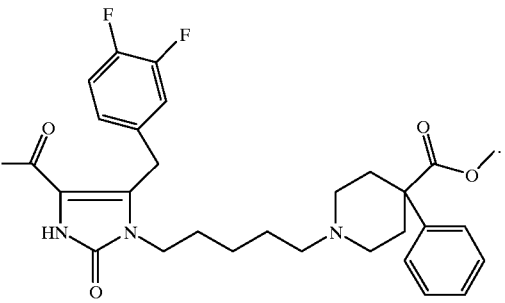

8. A pharmaceutical composition comprising a therapeutically effective amount of the compound of claim 1 and a pharmaceutically acceptable carrier.

9. The pharmaceutical composition of claim 8, wherein the amount of the compound is an amount from about 0.01 mg to about 800 mg.

10. The pharmaceutical composition of claim 9, wherein the amount of the compound is from about 0.01 mg to about 500 mg.

11. The pharmaceutical composition of claim 10, wherein the amount of the compound is from about 0.01 mg to about 250 mg.

12. The pharmaceutical composition of claim 11, wherein the amount of the compound is from about 0.1 mg to about 60 mg.

13. The pharmaceutical composition of claim 12, wherein the amount of the compound is from about 1 mg to about 20 mg.

14. The pharmaceutical composition of claim 8, wherein the carrier is a liquid and the composition is a solution.

15. The pharmaceutical composition of claim 8, wherein the carrier is a solid and the composition is a tablet.

16. The pharmaceutical composition of claim 8, wherein the carrier is a gel and the composition is a suppository.

17. The pharmaceutical composition of claim 8, wherein the compound additionally does not cause a fall in blood pressure at dosages effective to alleviate benign prostatic hyperplasia.

18. A method of treating a subject suffering from benign prostatic hyperplasia which comprises administering to the subject an amount of the compound of claim 1 effective to treat benign prostatic hyperplasia.

19. A method of claim 18, wherein the compound additionally does not cause a fall in blood pressure at dosages effective to alleviate benign prostatic hyperplasia.

20. The method of claim 19, wherein the compound effects treatment of benign prostatic hyperplasia by relaxing lower urinary tract tissue.

21. The method of claim 20, wherein lower urinary tract tissue is prostatic smooth muscle.

22. A method of treating a subject suffering from high intraocular pressure which comprises administering to the subject an amount of the compound of claim 1 effective to lower intraocular pressure.

23. A method of treating a subject suffering from a disorder associated with high cholesterol which comprises administering to the subject an amount of the compound of claim 1 effective to inhibit cholesterol synthesis.

24. A method of treating a subject suffering from cardiac arrhythmia which comprises administering to the subject an amount of the compound of claim 1 effective to treat cardiac arrhythmia.

25. A method of treating a subject suffering from impotency which comprises administering to the subject an amount of the compound of claim 1 effective to treat impotency.

26. A method of treating a subject suffering from sympathetically mediated pain which comprises administering to the subject an amount of the compound of claim 1 effective to treat sympathetically mediated pain.

27. A method of treating a subject suffering from migraine which comprises administering to the subject an amount of the compound of claim 1 effective to treat migraine.

28. A method of treating a disease which is susceptible to treatment by antagonism of the $\alpha_{1a}$ receptor which comprises administering to the subject an amount of the compound of claim 1 effective to treat the disease.

29. A method of treating a subject suffering from benign prostatic hyperplasia which comprises administering to the subject an amount of the compound of claim 1 in combination with a 5-alpha reductase inhibitor effective to treat benign prostatic hyperplasia.

30. The method of claim 29, wherein the 5-alpha reductase inhibitor is finasteride.

31. A pharmaceutical composition comprising a therapeutically effective amount of the compound of claim 1 in combination with a therapeutically effective amount of finasteride and a pharmaceutically acceptable carrier.

32. The pharmaceutical composition of claim 31, wherein the compound is present in an amount from about 0.01 mg to about 800 mg and the therapeutically effective amount of the finasteride is about 5 mg.

33. The pharmaceutical composition of claim 32, wherein the compound is present in an amount from about 0.1 mg to about 60 mg and the therapeutically effective amount of finasteride is about 5 mg.

34. The pharmaceutical composition of claim 33, wherein the compound is present in an amount from about 1 mg to about 20 mg and the therapeutically effective amount of finasteride is about 5 mg.

35. A method of relaxing lower urinary tract tissue which comprises contacting the lower urinary tract tissue with an amount of the compound of claim 1 effective to relax lower urinary tract tissue.

36. The method of claim 35, wherein the lower urinary tract tissue is prostatic smooth muscle.

37. A method of relaxing lower urinary tract tissue in a subject which comprises administering to the subject an amount of the compound of claim 1 effective to relax lower urinary tract tissue.

38. The method of claim 37, wherein the lower urinary tract tissue is prostatic smooth muscle.

39. A pharmaceutical composition made by combining a therapeutically effective amount of the compound of claim 1 and a pharmaceutically acceptable carrier.

40. A pharmaceutical composition made by combining a therapeutically effective amount of the compound of claim 1 with a therapeutically effective amount of finasteride and a pharmaceutically acceptable carrier.

41. A process for making a pharmaceutical composition comprising combining a therapeutically effective amount of the compound of claim 1 and a pharmaceutically acceptable carrier.

42. A process for making a pharmaceutical composition comprising combining a therapeutically effective amount of the compound of claim 1 with a therapeutically effective amount of finasteride and a pharmaceutically acceptable carrier.

* * * * *